(12) United States Patent
De La Torre-Bueno

(10) Patent No.: US 8,712,118 B2
(45) Date of Patent: Apr. 29, 2014

(54) AUTOMATED MEASUREMENT OF CONCENTRATION AND/OR AMOUNT IN A BIOLOGICAL SAMPLE

(75) Inventor: Jose De La Torre-Bueno, Carlsbad, CA (US)

(73) Assignee: Carl Zeiss Microimaging GmbH, Jena (DE)

( * ) Notice: Subject to any disclaimer, the term of this patent is extended or adjusted under 35 U.S.C. 154(b) by 538 days.

(21) Appl. No.: 12/455,391

(22) Filed: Jun. 1, 2009

(65) Prior Publication Data

US 2010/0007727 A1    Jan. 14, 2010

Related U.S. Application Data

(63) Continuation of application No. 10/822,561, filed on Apr. 8, 2004, now abandoned.

(60) Provisional application No. 60/462,159, filed on Apr. 10, 2003.

(51) Int. Cl.
*G06K 9/00*    (2006.01)

(52) U.S. Cl.
USPC ............ 382/128; 382/133; 382/162; 382/165

(58) Field of Classification Search
USPC .......................... 382/128, 133, 162, 165, 167
See application file for complete search history.

(56) References Cited

U.S. PATENT DOCUMENTS

| | | | |
|---|---|---|---|
| 3,824,393 A | 7/1974 | Brain et al. | |
| 3,851,972 A | 12/1974 | Smith et al. | |
| 4,090,243 A * | 5/1978 | Kotera et al. | 382/165 |
| 4,125,828 A | 11/1978 | Resnick et al. | |
| 4,513,438 A | 4/1985 | Graham et al. | |
| 4,673,973 A | 6/1987 | Ledley | |
| 4,700,298 A | 10/1987 | Palcic et al. | |
| 4,991,223 A | 2/1991 | Bradley | |
| 5,016,173 A | 5/1991 | Kenet et al. | |
| 5,085,325 A | 2/1992 | Jones et al. | |
| 5,202,931 A | 4/1993 | Bacus | |
| 5,231,580 A | 7/1993 | Cheung et al. | |
| 5,233,684 A | 8/1993 | Ulichney | |
| 5,257,182 A | 10/1993 | Luck et al. | |
| 5,287,272 A | 2/1994 | Rutenberg et al. | |
| 5,375,177 A | 12/1994 | Vaidyanathan et al. | |
| 5,428,690 A | 6/1995 | Bacus et al. | |
| 5,432,865 A | 7/1995 | Kasdan et al. | |
| 5,432,871 A | 7/1995 | Novik | |

(Continued)

FOREIGN PATENT DOCUMENTS

| | | |
|---|---|---|
| EP | 0 557 871 A2 | 9/1993 |
| EP | 0 713 086 A1 | 5/1996 |

(Continued)

OTHER PUBLICATIONS

U.S. Appl. No. 10/822,561, filed Apr. 8, 2004.

(Continued)

*Primary Examiner* — Brian Le
(74) *Attorney, Agent, or Firm* — Patterson Thuente Pedersen, P.A.

(57) ABSTRACT

Provided are methods, computer implemented methods, and devices for machine vision. The methods and devices are capable of quantifying the amount of a particular color resulting from a particular stain in a sample stained with multiple agents.

17 Claims, 9 Drawing Sheets

(56) References Cited

U.S. PATENT DOCUMENTS

| | | | |
|---|---|---|---|
| 5,449,622 A | 9/1995 | Yabe et al. | |
| 5,463,470 A | 10/1995 | Terashita et al. | |
| 5,473,706 A | 12/1995 | Bacus et al. | |
| 5,526,258 A | 6/1996 | Bacus | |
| 5,583,666 A | 12/1996 | Ellson et al. | |
| 5,585,469 A | 12/1996 | Kojima et al. | |
| 5,625,705 A | 4/1997 | Recht | |
| 5,635,402 A | 6/1997 | Alfano et al. | |
| 5,691,779 A | 11/1997 | Yamashita et al. | |
| 5,706,093 A | 1/1998 | Komiya | |
| 5,717,518 A | 2/1998 | Shafer et al. | |
| 5,732,150 A | 3/1998 | Zhou et al. | |
| 5,734,498 A | 3/1998 | Krasieva et al. | |
| 5,740,270 A | 4/1998 | Rutenberg et al. | |
| 5,799,105 A | 8/1998 | Tao | |
| 5,911,003 A | 6/1999 | Sones | |
| 6,007,996 A | 12/1999 | McNamara et al. | |
| 6,031,930 A | 2/2000 | Bacus et al. | |
| 6,058,322 A | 5/2000 | Nishikawa et al. | |
| 6,101,265 A | 8/2000 | Bacus et al. | |
| 6,215,892 B1 | 4/2001 | Douglass et al. | |
| 6,226,392 B1 | 5/2001 | Bacus et al. | |
| 6,313,452 B1 | 11/2001 | Paragano et al. | |
| 6,418,236 B1 | 7/2002 | Ellis et al. | |
| 6,453,060 B1 | 9/2002 | Riley et al. | |
| 6,456,734 B1 | 9/2002 | Youvan et al. | |
| 6,466,690 B2 | 10/2002 | Bacus et al. | |
| 7,065,236 B2 * | 6/2006 | Marcelpoil et al. | 382/133 |
| 2003/0138140 A1 | 7/2003 | Marcelpoil et al. | |
| 2004/0114227 A1 * | 6/2004 | Henderson et al. | 359/391 |

FOREIGN PATENT DOCUMENTS

| | | |
|---|---|---|
| WO | WO92/17848 | 10/1992 |
| WO | WO97/20198 | 6/1997 |
| WO | WO01/46657 A1 | 6/2001 |
| WO | WO03/025554 A2 | 3/2003 |

OTHER PUBLICATIONS

Ballard, et al., *Computer Vision*, Prentice-Hall, Inc., Englewood Cliffs, New Jersey, USA, 1982, pp. 65-70; and pp. 149-165.

Baxes, *Digital Image Processing*, John wiley & Sons, Inc., New York, NY, pp. 127-137.

* cited by examiner

US 8,712,118 B2

AUTOMATED MEASUREMENT OF CONCENTRATION AND/OR AMOUNT IN A BIOLOGICAL SAMPLE

CROSS REFERENCE TO RELATED APPLICATIONS

This application is a continuation of application Ser. No. 10/822,561, filed Apr. 8, 2004, which claims priority under 35 U.S.C. §119 from Provisional Application Ser. No. 60/462, 159, filed Apr. 10, 2003, both of which are incorporated herein by reference.

TECHNICAL FIELD

The disclosure relates to methods, computer implemented methods, and devices for machine vision. In particular the disclosure provides methods and devices that are capable of quantifying the amount of a particular color resulting from a particular stain in a sample stained with multiple agents.

BACKGROUND

Machine vision systems may be used to inspect objects based on their color(s). In industrial applications, such vision systems may inspect the colors of, for example, work pieces, produce, and color-coded pills. Such vision systems may also be used in medical applications to determine the composition of cells, in which different cell components are dyed different colors. Color may be an important indicator of whether a colored component is properly placed in a work piece, whether produce is ripe or overripe, whether a particular color-coded pill is in the proper location in its container, or whether a cell fits a criteria characteristic of a tumor cell.

SUMMARY

The disclosure provides a new method and system for transforming an image into a new color space in which each channel represents the absorption of light by one or more colors in a sample (e.g., one or more stains in a biological specimen).

The disclosure provides a method of quantifying a color in a sample comprising multiple colors, the method comprising measuring a color channel value in a plurality of pixels from a plurality of control samples comprising a single color of interest; defining a vector for each of the plurality of control samples, wherein each vector comprises an average of each color channel value present in the control; defining a matrix comprising each of the averages for each of the color channels; defining a conversion matrix comprising the inverse of the matrix based upon the control measurements; measuring color channel values in an image of an experimental sample comprising a plurality of colors of interest, each of the pixels comprising a plurality of color channels; and calculating the amount of a color in the experimental sample by converting the channel values in the experimental sample using the conversion matrix. In one aspect, the method is implemented by a computer.

The disclosure also provides A computer program on computer readable medium comprising instructions to cause a computer to measure a color channel value in a plurality of pixels from a plurality of control samples comprising a single color of interest; define a vector for each of the plurality of control samples, wherein each vector comprises an average of each color channel value present in the control; define a matrix comprising each of the averages for each of the color channels; define a conversion matrix comprising the inverse of the matrix based upon the control measurements; measure color channel values in an image of an experimental sample comprising a plurality of colors of interest, each of the pixels comprising a plurality of color channels; calculating the amount of a color in the experimental sample by converting the channel values in the experimental sample using the conversion matrix; and outputting the amount of a color in the experimental sample.

The disclosure further provides a machine vision system for automated analysis of a biological sample on a slide comprising:
a computer comprising:
 a system processor;
 a computer program on computer readable medium, the computer program comprising an image algorithm comprising instructions to cause the computer to:
  measure a color channel value in a plurality of pixels from a plurality of control samples comprising a single color of interest;
  define a vector for each of the plurality of control samples, wherein each vector comprises an average of each color channel value present in the control;
  define a matrix comprising each of the averages for each of the color channels;
  define a conversion matrix comprising the inverse of the matrix based upon the control measurements;
  measure color channel values in an image of an experimental sample comprising a plurality of colors of interest, each of the pixels comprising a plurality of color channels;
  calculating the amount of a color in the experimental sample by converting the channel values in the experimental sample using the conversion matrix; and
  outputting the amount of a color in the experimental sample;
a monitor in operable communication with the computer; and
 an input device in communication with the computer,
 an optical system in operable communication with the computer, comprising
  a movable stage;
  an automated loading and unloading member for loading and unloading of a slide;
  an identification member;
  an optical sensing array in optical communication with the stage configured to acquire an image at a location on a slide and in electrical communication with the processor;
  a storage member for storing the location of a candidate object or area of interest; and
  a storage device for storing each image.

The disclosure provides a method of determining cell ratio is a biological sample comprising calculating a ratio of positively stained cells in a sample to the total number of cells of a specified type in the sample, wherein the number of positively stained cells is determined by measuring the pixels of a first color in a digital image comprising a plurality of pixels corresponding to the sample for a marker-specific stain divided by the total area of a field of view corresponding to the digital image, and wherein the number of total cells of a specified type is calculated by measuring the number of pixels of a reference color in a digital image comprising a plurality of pixels corresponding to the sample for cell-type stain divided by the total area of a field of view corresponding to the digital image; and comparing the ratio to a control ratio determined with known positive to specified cell types. In one aspect, this method is implemented by a computer. In another aspect, the disclosure provides an automated imaging system comprising the computer-implemented method.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

The above and other features of the disclosure including various details of construction and combinations of parts will now be more particularly described with reference to the accompanying drawings and pointed out in the claims. It will be understood that the particular apparatus embodying the disclosure is shown by way of illustration only and not as a limitation of the disclosure. The principles and features of this disclosure may be employed in varied and numerous embodiments without departing from the scope of the disclosure.

DETAILED DESCRIPTION

Figure 1:
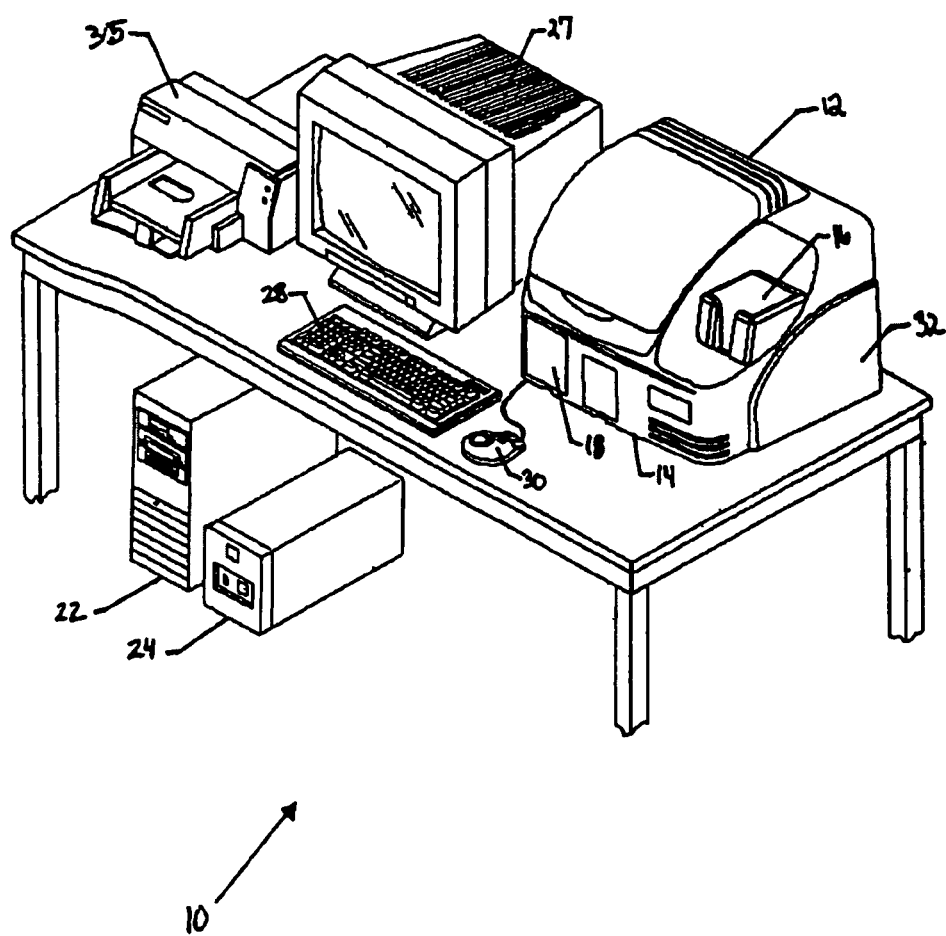
FIG. 1 is a perspective view of an exemplary apparatus for automated cell analysis embodying the disclosure.

Pixels in digital images may have one of thousands, even millions, of possible color values (e.g., 16 bit and 24 bit color). Machine vision systems may be interested in ranges of related color values, which fall between upper and lower thresholds. These ranges of color values may be referred to as keyed colors. Transforming a raw pixel color value to a keyed color may simplify downstream processing in the vision system.

The biological mechanisms of many diseases have been clarified by microscopic examination of tissue samples. Histopathological examination has also permitted the development of effective medical treatments for a variety of illnesses. In standard anatomical pathology, a diagnosis is made on the basis of cell morphology and staining characteristics. Tumor samples, for example, can be examined to characterize the tumor type and suggest whether the patient will respond to a particular form of chemotherapy. Microscopic examination and classification of tissue samples stained by standard methods (such as hematoxylin and eosin) has improved cancer treatment significantly. Even with these advancements many cancer treatments are ineffective. This is due to the fact that many cancers are the result of changes in cellular machinery that provides the phenotypic changes resulting in aberrant cellular proliferation. Thus, due to the diverse nature of the changes that cause various cancers, a cancer condition caused by one cellular mechanism may be treatable by one therapeutic regimen, while a similar cancer, if caused by a different cellular mechanism requires a different therapeutic regimen.

Recent advances in molecular medicine have provided an even greater opportunity to understand the cellular mechanisms of disease, and select appropriate treatments with the greatest likelihood of success. For example, some hormone dependent breast tumor cells have an increased expression of estrogen receptors indicating that the patient from whom the tumor was taken will likely respond to certain anti-estrogen drug treatments. Other diagnostic and prognostic cellular changes include the presence of tumor specific cell surface antigens (as in melanoma), the production of embryonic proteins (such as carcinoembryonic glycoprotein antigen produced by gastrointestinal tumors), and genetic abnormalities (such as activated oncogenes in tumors). A variety of techniques have evolved to detect the presence of these cellular abnormalities, including immunophenotyping with monoclonal antibodies, in situ hybridization using nucleic acid probes, and DNA amplification using the polymerase chain reaction (PCR).

Effective use of such markers in assisting in the diagnosis and identification of an effective therapeutic regimen has been impeded by the inability of current automated analysis systems to utilize and identify the varied markers in a cost efficient, time sensitive, and reproducible manner. Thus, previous techniques and systems have often proven inadequate for the efficient analysis of tissue samples requiring a rapid parallel analysis of a variety of independent microscopic, histological and/or molecular characteristics.

The methodology of measuring the amount of a light absorbing stain in an area by transmission microscopy is known. A derivation of the formula is given here for background. The formulas given below work equally well for single pixels or integrated areas.

Define:
%T=% transmission
I=illumination light intensity
P=transmitted light intensity
G=camera gain
C=concentration in users units
k=% transmission of 1 unit of concentration in some unit
l=conversion of user units to units in above measure
R=system reading in system units (possibly an arbitrary scale)
R=G log(P) (assuming camera gamma is on)
P=I·%T
%T=$k^{-lC}$
R=G log(I·%T)
R=G log(I·$k^{-lC}$)
R=G (log I+log($k^{-lC}$)
R=G log(I)+G log($k^{-lC}$). By definition $R_o$=G log(I)

$$R = R_o + G\log(k^{-lC})$$

$$R = R_o + G \cdot (-lC)\log(k)$$

$$R - R_o = G \cdot (-lC)\log(k)$$

$$R - R_o = -C(Gl\log(k))$$

Define $\alpha = Gl\log(k)$ $$R - R_o = -C \cdot \alpha$$

$$\frac{R_o - R}{A} = C$$

Therefore if we know $R^c$ at known concentration $C^c$ we can define:

$$\alpha = \frac{R_o - R^c}{C^c}$$

Therefore $$C = \frac{(R_o - R)C^c}{(R_o - R_c)}$$

(i.e. concentration is a linear function of R) Accordingly, it follows that if one has a 0 control and one other control one does not need to know:
G the camera gain
I the illumination intensity
k the standard % transmission of stain
l the conversion of standard concentration to the working concentration units.

Where a sample comprises many stains or colors to detect and/or where one wishes to measure some pixels or larger areas for all the stains or colors present, the formulae above will not work. This is due, in part, because of the stains or colors spectral curves may overlap resulting in a loss of transmission due to one stain/color or another.

The disclosure provides a new method and system for transforming an image into a new color space in which each channel represents the absorption of light by one or more colors in a sample (e.g., one or more stains in a biological specimen).

The methods of the disclosure can be implemented in a computer program on a computer readable medium. Such methods and computer programs can be utilized in conjunction with machine vision systems such as, for example, the ACIS™ automated microscope system (ChromaVision Medical Systems, Inc., San Juan Capistrano, Calif.). The disclosure provides a new method and system for transforming an image into a new color space in which each channel represents the absorption of light by one of the stains.

The disclosure can be described by reference to the following example that described the analysis of a medical microscope slide stained with multiple stains. However, it will be recognized by those skilled in the art that the implementation of the methods and computer programs can be used for any number of machine vision techniques that require the measurement of multiple colors in a sample.

If the white of a clear space on the glass of a microscope slide or other sample is defined as: $W=(r_w, g_w, b_w)$, a new color space C can be defined as: $C=(r_w-r, g_w-g, b_w-b)$. Using 3 control samples (e.g., slides) each comprising a color (e.g., a stain) with one of the colors (stains) to be measured (called K, λ and C) and an experimental sample (e.g., a slide) comprising all 3 colors (e.g., all the stains) on which a sample to be measured is contained, the concentration of each color (e.g., stain) at each pixel can be measured using the following method.

For each control a vector of the average r, g and b values of all pixels is defined:

$$\overline{K} = (\overline{r}_K, \overline{g}_K, \overline{b}_K)$$

$$\overline{\lambda} = (\overline{r}_\lambda, \overline{g}_\lambda, \overline{b}_\lambda)$$

$$\overline{c} = (\overline{r}_c, \overline{g}_c, \overline{b}_c)$$

The matrix is then defined as:

$$Q \equiv \begin{pmatrix} \overline{r}_K & \overline{r}_\lambda & \overline{r}_c \\ \overline{g}_K & \overline{g}_\lambda & \overline{g}_c \\ \overline{b}_K & \overline{b}_\lambda & \overline{b}_c \end{pmatrix}$$

iff $det(Q) \neq 0$

Then Q is invertible and the 3 colors (e.g., stains) are genuinely different colors (as opposed to shades of the same color). The magnitude of det(Q) is inversely proportional to the noise the presence of each of the colors (e.g., stains) imposes on an attempt to measure another using this method. Where a sample comprises a fluorescent images, the values of r, g, and b (e.g., the color channel) are the absolute values and not an average. In addition:

$$\overline{k}, \overline{\lambda}, \overline{c}$$

Forms a basis of a new color space E and P; $Q^{-1}$ is a transform from C to E.

Therefore for any pixel (r,g,b) in C on the experimental sample (e.g., slide)

$$\begin{pmatrix} k \\ l \\ c \end{pmatrix} = P \begin{pmatrix} r \\ g \\ b \end{pmatrix}$$

can be calculated. Where k will be proportional to the concentration of color (e.g., stain) K; l will be proportional to the concentration of color (e.g., stain) λ; and c will be proportional to the concentration of color (e.g., stain) C.

The IOD of some area of the sample (e.g., a slide, for instance, a cell or area of tissue on the slide) measured in one of these new channels will be proportional to the amount of the corresponding color (e.g., stain) in that area. Using a control, a conversion factor can be calculated by the methods described above and used to directly and independently determine the amount of the 3 colors in the sample (e.g., stains in the sample).

Furthermore for any pixel on the image of the experimental sample (e.g., slide):

$$\begin{pmatrix} r' \\ g' \\ b' \end{pmatrix} = Q \begin{pmatrix} k \\ 0 \\ 0 \end{pmatrix}$$

can be calculated by substituting 0 for the values of 2 of the colors (e.g., stains) and converting back to the original color space:

$$\begin{pmatrix} r'_o \\ g'_o \\ b'_o \end{pmatrix} = \begin{pmatrix} r_w - r' \\ g_w - g' \\ b_w - b' \end{pmatrix}$$

The resulting values will be the appearance the pixel would have had if those 2 colors (e.g., stains) had not been used. Using the above algorithm and method an image that shows what the sample (e.g., slide) would have looked like if one or two of the colors/stains had not been used can be produced. In some aspects, a color/stain may be so dark that some pixels have a reading of 0.

In another embodiment of the disclosure, the method and system includes an extension to the method used to measure cell ratios based on counts of pixels in stained nuclei. In this context a sub-cellular compartment (e.g., a portion of a cell such as the nucleus, cytoplasm or membrane). In many diagnostic assays and experiments the ratio of cells stained for a certain target molecule as a fraction of all cells of a certain specified type in a given region needs to be established.

To understand the applicability of this method of the disclosure the following example is used. For example, 2 stains one of which marks the target molecule and another reference stain which marks all cells of the specified type (regardless of whether they have the target molecule) is used on a sample. A ratio between the target molecule and the cell marker is used in medical diagnosis. The ratio is calculated even if the target molecule is found in one sub-cellular compartment (e.g., a portion of a cell such as the nucleus, cytoplasm or membrane) and the reference marker for identifying cells of the specified type is found in another sub-cellular compartment. Thus, let:

$N_p$=# of positive cells
$N_r$=total # of cells of specified type (i.e. all cells labeled in the reference compartment)
$a_p$=Average area of compartment labeled in positive cells
$a_r$=Average area of reference compartment labeled in all cells of the specified type
$P_p$=Number of pixels of positive color (labeling target molecule)
$P_r$=Number of pixels of reference color (labeling cells of the specified type)
Using the above definitions one can calculate the desired ratio:

$$R = \frac{N_p}{N_r}$$

As follows:

$$N_p = \frac{P_p}{a_p}$$

$$N_r = \frac{P_r}{a_r}$$

$$R = \frac{N_p}{N_r} = \frac{P_p a_r}{P_r a_p}$$

$$R^c = \frac{P_p^c a_r}{P_r^c a_p}$$

Where the superscript $c$ indicates the corresponding value when measuring a control area with a known ratio.

$$\frac{a_r}{a_p} = R^c \frac{P_r^c}{P_p^c}$$

$$\therefore R = \frac{P_p R^c P_r^c}{P_r P_p^c}$$

This shows that if an area with known ratio of positive to specified type cells is known one can determine the ratio in another area from the ratios of stained pixels. This is true even if the positive cells are being recognized on the basis of a stain that marks a different compartment than the stain that marks all cells of the specified type.

The various techniques, methods, and aspects of the disclosure described above can be implemented in part or in whole using computer-based systems and methods. Additionally, computer-based systems and methods can be used to augment or enhance the functionality described above, increase the speed at which the functions can be performed, and provide additional features and aspects as a part of, or in addition to, those of the disclosure described elsewhere in this document. Various computer-based systems, methods and implementations in accordance with the above-described technology are presented below.

A processor-based system for carrying out a method of the disclosure can include a main memory, typically random access memory (RAM), and can also include a secondary memory. The secondary memory can include, for example, a hard disk drive and/or a removable storage drive, representing a floppy disk drive, a magnetic tape drive, an optical disk drive, and the like. The removable storage drive reads from and/or writes to a removable storage medium. Removable storage medium refers to a floppy disk, magnetic tape, optical disk, and the like, which is read by, and written to by, a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between a computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

A computer program medium and computer usable medium are used to refer generally to media such as a removable storage device, a disk capable of installation in a disk drive, and signals on a channel. These computer program products are means for providing software or program instructions to a computer system.

Computer programs (sometimes referred to as computer control logic) are stored in main memory and/or secondary memory. Computer programs can also be received via a communications interface. Such computer programs, when executed, enable the computer system to perform the features of the disclosure as discussed herein. In particular, the computer programs, when executed, enable the processor to perform the features of the disclosure. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the disclosure as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the disclosure. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the disclosure to launch an application to, for example, perform an analysis according to the disclosure.

Although the application of the above described methods and algorithms can be implemented on various machine vision systems, the application will be described herein with reference to an automated microscope system (although one of skill in the art will recognize the applicability to many similar systems).

The disclosure provides an automated analysis system that quickly and accurately scans large amounts of biological material on a slide. In addition, the system automates the analysis of fluorescent and transmitted light images on a slide quickly and accurately. Accordingly, the disclosure provides useful methods, apparatus, and systems for use in research and patient diagnostics to locate cell objects for analysis having a plurality of non-fluorescent stains and/or fluorescent indicators.

A biological sample and/or subsample comprises biological materials obtained from or derived from a living organism. Typically a biological sample will comprise proteins, polynucleotides, organic material, cells, tissue, and any combination of the foregoing. Such samples include, but are not limited to, hair, skin, tissue, cultured cells, cultured cell media, and biological fluids. A tissue is a mass of connected cells and/or extracellular matrix material (e.g., CNS tissue, neural tissue, eye tissue, placental tissue, mammary gland tissue, gastrointestinal tissue, musculoskeletal tissue, genitourinary tissue, and the like) derived from, for example, a human or other mammal and includes the connecting material and the liquid material in association with the cells and/or tissues. A biological fluid is a liquid material derived from, for example, a human or other mammal. Such biological fluids include, but are not limited to, blood, plasma, serum, serum derivatives, bile, phlegm, saliva, sweat, amniotic fluid, mammary fluid, and cerebrospinal fluid (CSF), such as lumbar or ventricular CSF. A sample also may be media containing cells or biological material.

A biological sample may be embedded in embedding media such as paraffin or other waxes, gelatin, agar, polyethylene glycols, polyvinyl alcohol, celloidin, nitrocelluloses, methyl and butyl methacrylate resins or epoxy resins, which are polymerized after they infiltrate the specimen. Water-soluble embedding media such as polyvinyl alcohol, carbowax (polyethylene glycols), gelatin, and agar, may be used directly on specimens. Water-insoluble embedding media such as paraffin and nitrocellulose require that specimens be dehydrated in several changes of solvent such as ethyl alcohol, acetone, or isopropyl alcohol and then be immersed in a solvent in which the embedding medium is soluble. In the case where the embedding medium is paraffin, suitable solvents for the paraffin are xylene, toluene, benzene, petroleum, ether, chloroform, carbon tetrachloride, carbon bisulfide, and cedar oil. Typically a tissue sample is immersed in two or three baths of the paraffin solvent after the tissue is dehydrated and before the tissue sample is embedded in paraffin. Embedding medium includes, for examples, any synthetic or natural matrix suitable for embedding a sample in preparation for tissue sectioning.

A tissue sample may be a conventionally fixed tissue sample, tissue samples fixed in special fixatives, or may be an unfixed sample (e.g., freeze-dried tissue samples). If a tissue sample is freeze-dried, it should be snap-frozen. Fixation of a tissue sample can be accomplished by cutting the tissue specimens to a thickness that is easily penetrated by fixing fluid. Examples of fixing fluids are aldehyde fixatives such as formaldehyde, formalin or formal, glyoxal, glutaraldehyde, hydroxyadipaldehyde, crotonaldehyde, methacrolein, acetaldehyde, pyruic aldehyde, malonaldehyde, malialdehyde, and succinaldehyde; chloral hydrate; diethylpyrocarbonate; alcohols such as methanol and ethanol; acetone; lead fixatives such as basic lead acetates and lead citrate; mercuric salts such as mercuric chloride; formaldehyde sublimates; sublimate dichromate fluids; chromates and chromic acid; and picric acid. Heat may also be used to fix tissue specimens by boiling the specimens in physiologic sodium chloride solution or distilled water for two to three minutes. Whichever fixation method is ultimately employed, the cellular structures of the tissue sample must be sufficiently hardened before they are embedded in a medium such as paraffin.

Using techniques such as those disclosed herein, a biological sample comprising a tissue may be embedded, sectioned, and fixed, whereby a single biopsy can render a plurality of subsamples upon sectioning. In one aspect, a plurality of subsamples corresponding to the number of stains to be used in a particular assay are treated with a single stain (i.e. as controls) and a subsample is then treated with a plurality of stains. As discussed below, such subsamples can be examined under different staining or fluorescent conditions thereby rendering a wealth of information about the tissue biopsy. In one aspect of the disclosure, an array of tissue samples may be prepared and located on a single slide. The generation of such tissue-microarrays are known in the art. Each tissue sample in the tissue-microarray may be stained and/or treated the same or differently using both automated techniques and manual techniques (see, e.g., Kononen et al. Nature Medicine, 4(7), 1998; and U.S. Pat. No. 6,103,518, the disclosures of which are incorporated herein by reference).

In another aspect, the disclosure provides a method whereby a single biological sample may be assayed or examined in many different ways. Under such conditions a sample may be stained or labeled with a plurality of reagents.

The disclosure provides methods of automated analysis of a biological sample. The biological sample and/or subsample can be contacted with a variety of reagents useful in determining and analyzing cellular molecules and mechanisms. Such reagents include, for example, polynucleotides, polypeptides, small molecules, and/or antibodies useful in in situ screening assays for detecting molecules that specifically bind to a marker present in a sample. Such assays can be used to detect, prognose, diagnose, or monitor various conditions, diseases, and disorders, or monitor the treatment thereof. A reagent can be detectably labeled such that the agent is detectable when bound or hybridized to its target marker or ligand. Such means for detectably labeling any of the foregoing reagents include an enzymatic, fluorescent, or radionuclide label. Other reporter means and labels are well known in the art. As used herein the term "stain" refers a detectable label which may be a colored precipitate, a chromogenic molecule, a fluorescent molecule, and the like.

A marker can be any cell component present in a sample that is identifiable by known microscopic, histologic, or molecular biology techniques. Markers can be used, for example, to distinguish neoplastic tissue from non-neoplastic tissue. Such markers can also be used to identify a molecular basis of a disease or disorder including a neoplastic disease or disorder. Such a marker can be, for example, a molecule present on a cell surface, an overexpressed target protein or nucleic acid, a nucleic acid mutation or a morphological characteristic of a cell present in a sample.

A reagent useful in the methods of the disclosure can be an antibody. Antibodies useful in the methods of the disclosure include intact polyclonal or monoclonal antibodies, as well as fragments thereof such as Fab and F(ab')2. For example, monoclonal antibodies are made from antigen containing fragments of a protein by methods well known to those skilled in the art (Kohler, et al., Nature, 256:495, 1975). Fluorescent molecules may be bound to an immunoglobulin either directly or indirectly by using an intermediate functional group. Enzyme labels can also be functionally attach whereby the enzyme acts on chromogenic substrates to render a colored precipitate at the location of the target marker.

A reagent useful in the methods of the disclosure can also be a nucleic acid molecule (e.g., an oligonucleotide or polynucleotide). For example, in situ nucleic acid hybridization techniques are well known in the art and can be used to identify an RNA or DNA marker present in a sample or subsample. Screening procedures that rely on nucleic acid hybridization make it possible to identify a marker from any sample, provided the appropriate oligonucleotide or polynucleotide agent is available. For example, oligonucleotide agents, which can correspond to a part of a sequence encoding a target polypeptide (e.g., a cancer marker comprising a polypeptide), can be synthesized chemically or designed through molecular biology techniques. The polynucleotide encoding the target polypeptide can be deduced from the genetic code, however, the degeneracy of the code must be taken into account. For such screening, hybridization is typically performed under in situ conditions known to those skilled in the art.

Figure 2:
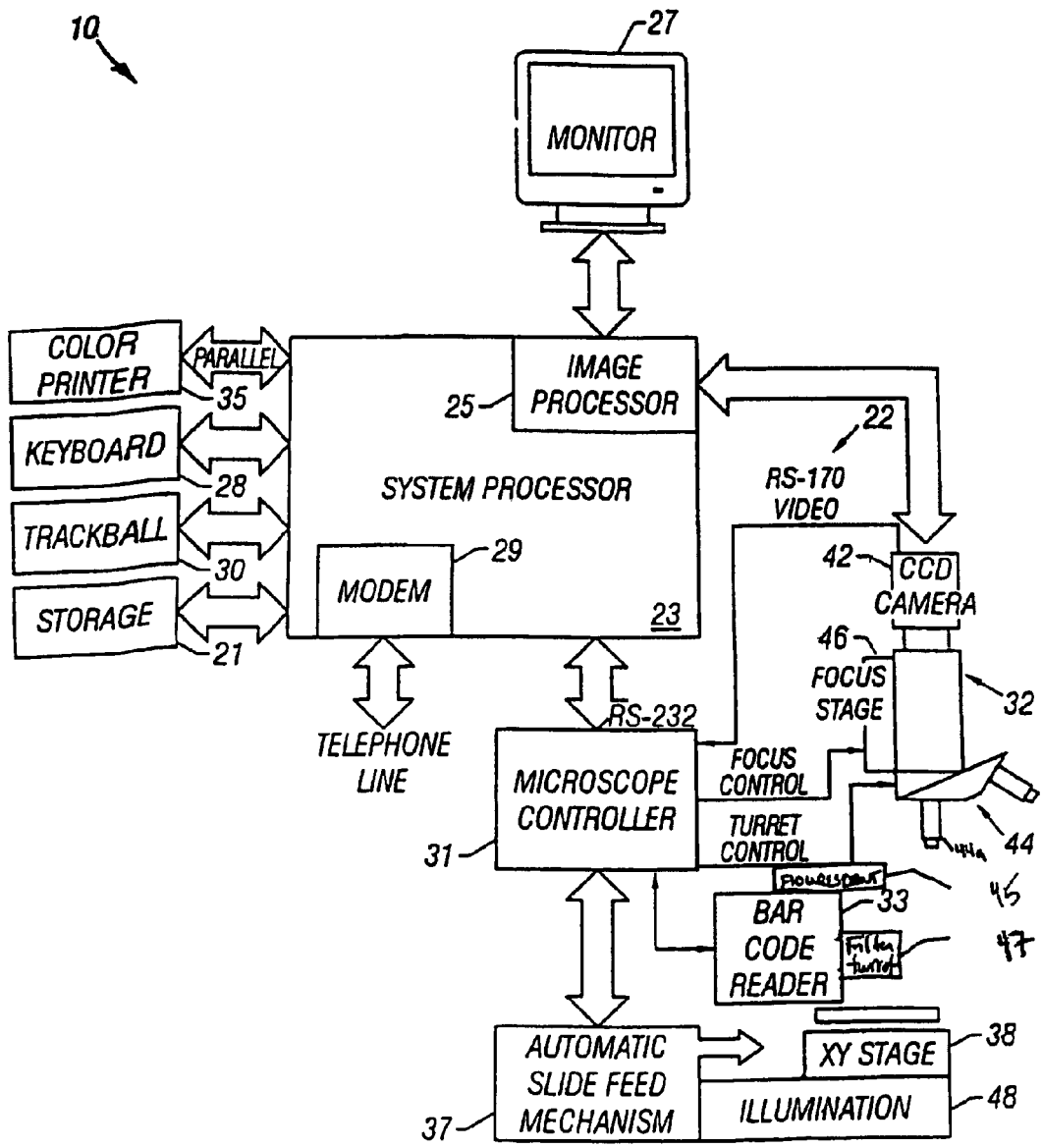
FIG. 2 is a block diagram of the apparatus shown in FIG. 1.

Referring now to FIGS. 1 and 2, a machine vision apparatus for automated cell analysis of biological samples is generally indicated by reference numeral 10 as shown in perspective view in FIG. 1 and in block diagram form in FIG. 2. The apparatus 10 comprises a microscope subsystem 32 housed in a housing 12. The housing 12 includes a slide carrier input hopper 16 and a slide carrier output hopper 18. A door 14 in the housing 12 secures the microscope subsystem from the external environment. A computer subsystem comprises a computer 22 having at least one system processor 23, and a communications modem 29. The computer subsystem further includes a computer/image monitor 27 and other external peripherals including storage device 21, a pointing device, such as a track ball or mouse device 30, a user input device, such as a touch screen, keyboard, or voice recognition unit 28 and color printer 35. An external power supply 24 is also shown for power outage protection. The apparatus 10 further includes an optical sensing array 42, such as, for example, a CCD camera, for acquiring images. Microscope movements are under the control of system processor 23 through a number of microscope-subsystem functions described further in detail. An automatic slide feed mechanism in conjunction with X-Y stage 38 provide automatic slide handling in the apparatus 10. An illuminator 48 comprising a bright field transmitted light source projects light onto a sample on the X-Y stage 38, which is subsequently imaged through the microscope subsystem 32 and acquired through optical sensing array 42 for processing by the system processor 23. A Z stage or focus stage 46 under control of the system processor 23 provides displacement of the microscope subsystem in the z plane for focusing. The microscope subsystem 32 further includes a motorized objective turret 44 for selection of objectives.

The apparatus 10 may also include a fluorescent excitation light source 45 and may further include a plurality of fluorescent filters on a turret or wheel 47. Alternatively, a filter wheel may have an electronically tunable filter. In one aspect, fluorescent excitation light from fluorescent excitation light source 45 passes through fluorescent filter 47 and proceeds to contact a sample on the XY stage 38. Fluorescent emission light emitted from a fluorescent agent contained on a sample passes through objective 44a to optical sensing array 42. The fluorescent emission light forms an image, which is digitized by an optical sensing array 42, and the digitized image is sent to an image processor 25 for subsequent processing.

The purpose of the apparatus 10 is for the automatic scanning of prepared microscope slides for the detection of candidate objects of interest such as normal and abnormal cells, e.g., tumor cells. In one aspect, the apparatus 10 is capable of detecting rare events, e.g., event in which there may be only one candidate object of interest per several hundred thousand objects, e.g., one to five candidate objects of interest per 2 square centimeter area of the slide. The apparatus 10 automatically locates and can count candidate objects of interest noting the coordinates or location of the candidate object of interest on a slide based upon color, size and shape characteristics. A number of stains can be used to stain candidate objects of interest and other objects (e.g., normal cells) different colors so that such cells can be distinguished from each other (as described herein).

A biological sample may be prepared with one or more reagent to obtain a colored insoluble precipitate. As one step in the methods and systems of the disclosure an apparatus 10 is used to detect a combination of colored precipitates as a candidate object or area of interest. During operation of the apparatus 10, a pathologist or laboratory technician mounts slides onto slide carriers. Each slide may contain a single sample or a plurality of samples (e.g., a tissue microarray). Each slide carrier can be designed to hold a number of slides from about 1-50 or more. A number of slide carriers are then loaded into input hopper 16 (see FIG. 1). The operator can specify the size, shape and location of the area to be scanned or alternatively, the system can automatically locate an area. The operator then commands the system to begin automated scanning of the slides through a graphical user interface. Unattended scanning begins with the automatic loading of the first carrier and slide onto the precision motorized X-Y stage 38. In one aspect of the disclosure, a bar code label affixed to the slide or slide carrier is read by a bar code reader 33 during this loading operation. Each slide is then scanned or imaged at a desired magnification, for example, 4× or 10×, to identify candidate cells or objects of interest based on their color, size and shape characteristics. The term "coordinate" or "address" is used to mean a particular location on a slide or sample. The coordinate or address can be identified by any number of means including, for example, X-Y coordinates, r-o coordinates, polar, vector or other coordinate systems known in the art. In one aspect of the disclosure a slide is scanned under a first parameter comprising a desired magnification and using a bright field light source from illuminator 48 (see FIG. 2) to identify a candidate cell or object of interest.

The methods, systems, and apparatus of the disclosure may obtain a low magnification image of a candidate cell or object of interest and then return to each candidate cell or object of interest based upon the previously stored coordinates to reimage and refocus at a higher magnification such as 40× or to reimage under fluorescent conditions. To avoid missing candidate cells or objects of interest, the system can process low magnification images by reconstructing the image from individual fields of view and then determine objects of interest. In this manner, objects of interest that overlap more than one objective field of view may be identified. In some aspects, a single low magnification image is acquired that is at a sufficiently low magnification that the whole (or a substantial portion thereof, e.g. 70%-99%) of the sample is imaged at one time. The apparatus comprises a storage device 21 that can be used to store an image of a candidate cell or object of interest for later review by a pathologist or to store identified coordinates for later use in processing the sample or a subsample. The storage device 21 can be a removable hard drive, DAT tape, local hard drive, optical disk, or may be an external storage system whereby the data is transmitted to a remote site for review or storage. In one aspect, stored images (from both fluorescent and bright field light) can be overlapped and/or viewed in a mosaic of images for further review (as discussed more fully herein).

Apparatus 10 may also be used for fluorescent imaging (e.g., in FISH techniques) of prepared microscope slides for the detection of candidate objects of interest such as normal and abnormal cells, e.g., tumor cells. Similar techniques as those described above for image acquisition and processing are used with the caveat that a fluorescence excitation light source 45 and filters are used rather than transmitted light. In this aspect, the slide has been contacted with a fluorescent reagent labeled with a fluorescent indicator. The fluorescent reagent is an antibody, polypeptide, oligonucleotide, or polynucleotide labeled with a fluorescent indicator. A number of fluorescent indicators are known in the art and include DAPI, Cy3, Cy3.5, Cy5, Cy5.5, Cy7, umbelliferone, fluorescein, fluorescein isothiocyanate (FITC), rhodamine, dichlorotriazinylamine fluorescein, dansyl chloride or phycoerythrin. In another aspect of the disclosure a luminescent material may be used. Useful luminescent materials include luminol; examples of bioluminescent materials include luciferase, luciferin, and aequorin.

A fluorescent indicator should have distinguishable excitation and emission spectra. Where two or more fluorescent indicators are used they should have differing excitation and emission spectra that differ, respectively, by some minimal value (typically about 15-30 nm). The degree of difference will typically be determined by the types of filters being used in the process. Typical excitation and emission spectra for DAPI, FITC, Cy3, Cy3.5, Cy5, Cy5.5, and Cy7 are provided below:

| Fluorescent indicator | Excitation Peak | Emission Peak |
|---|---|---|
| DAPI | 350 | 450 |
| FITC | 490 | 520 |
| Cy3 | 550 | 570 |
| Cy3.5 | 580 | 595 |
| Cy5 | 650 | 670 |
| Cy5.5 | 680 | 700 |
| Cy7 | 755 | 780 |

A biological sample is prepared with one or more fluorescently labeled reagents or luminescently labeled reagents to identify molecules of interest within the biological sample. An apparatus of the disclosure is used to detect the fluorescence or luminescence of the molecule when exposed to a wavelength that excites a fluorescent indicator attached to the fluorescent reagent or exposed to conditions that allow for luminescence. The automated system of the disclosure scans a biological sample contacted with a fluorescently reagent under conditions such that a fluorescent indicator attached to the agent fluoresces, or scans a biological sample labeled with a luminescent agent under conditions that detects light emissions from a luminescent indicator. Examples of conditions include providing a fluorescent excitation light that contacts and excites the fluorescent indicator to fluoresce. As described in more detail herein the apparatus of the disclosure includes a fluorescent excitation light source and can also include a number of fluorescent excitation filters to provide different wavelengths of excitation light. In one aspect of the disclosure, a bar code label affixed to a slide or slide carrier is read by a bar code reader 33 during a loading operation. The bar code provides the system with information including, for example, information about the scanning parameters including the type of light source or the excitation light wavelength to use. Each slide is then scanned at a desired magnification, for example, 10×, to identify candidate cells or objects or areas of interest based on their color, size, and shape characteristics. Where the location of candidate cells or objects or areas of interest have been previously identified, the location, coordinate, or address of the candidate cells or objects or area of interest (including corrected coordinates where more than one subsample is analyzed) are used to focus the system at those specific locations and obtain fluorescent or bioluminescent images.

The methods, system, and apparatus of the disclosure can obtain a first image using a transmitted light source at either a low magnification or high magnification of a candidate cell or object or area of interest and then return to the coordinates (or corrected coordinates) associated with each candidate cell or object of interest in the same sample or a related subsample to obtain a fluorescent image. Fluorescent images or luminescent images can be stored on a storage device 21 that can be used to store an image of a candidate cell or object or area of interest for later review by a pathologist. The storage device 21 can be a removable hard drive, DAT tape, local hard drive, optical disk, or may be an external storage system whereby the data is transmitted to a remote site for review or storage. In one aspect, stored images (from both fluorescent and bright field light) can be overlapped and/or viewed in a mosaic of images for further review (as discussed more fully herein).

Where transmitted light microscopy or fluorescent light microscopy are followed sequentially in either order the light sources for both processes must be managed. Such light source management is performed using the system processor 23 through the fluorescent controller 102 and illumination controller 106 (see, FIG. 3). During processing of images in transmitted light microscopy the fluorescent excitation light source is off or blocked such that excitation light from the fluorescent light source does not contact the sample. When fluorescent images are being obtained the transmitted light source is off or blocked such that the transmitted light does not pass through the sample while the sample is contacted by fluorescent excitation light from fluorescent excitation light source 45.

Figure 3:
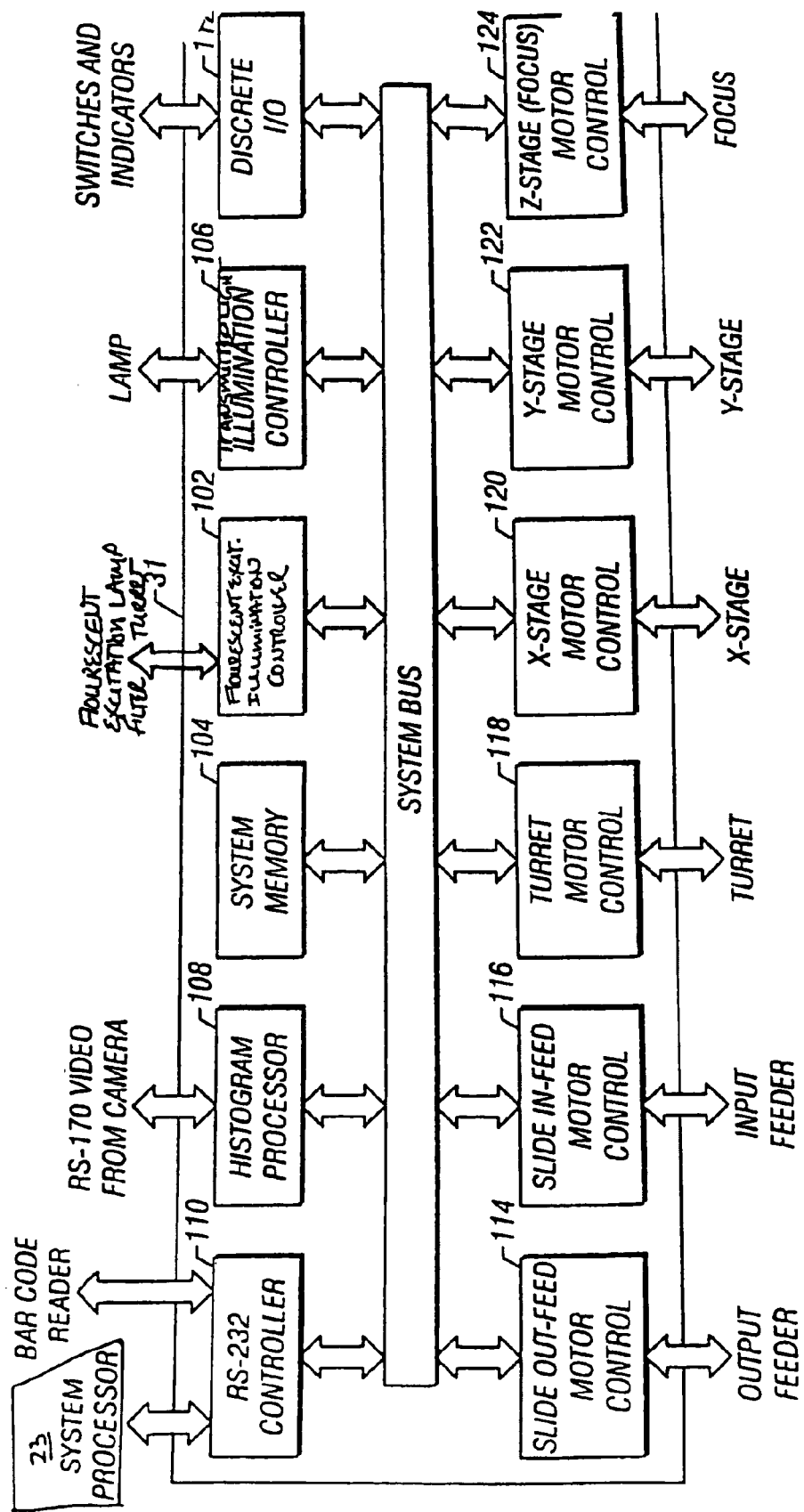
FIG. 3 is a block diagram of the system processor of FIG. 2.

Having described the overall operation of the apparatus 10 from a high level, the further details of the apparatus will now be described. Referring to FIG. 3, the microscope controller 31 is shown in more detail. The microscope controller 31 includes a number of subsystems. The apparatus system processor 23 controls these subsystems. The system processor 23 controls a set of motor-control subsystems 114 through 124, which control the input and output feeder, the motorized turret 44, the X-Y stage 38, and the Z stage 46 (FIG. 2). The system processor 23 further controls a transmitted light illumination controller 106 for control of substage illumination 48 bright field transmitted light source and controls a fluorescent excitation illumination controller 102 for control of fluorescent excitation light source 45 and/or filter turret 47. The transmitted light illumination controller 106 is used in conjunction with camera and image collection adjustments to compensate for the variations in light level in various samples. The light control software samples the output from the camera at intervals (such as between loading of slide carriers), and commands the transmitted light illumination controller 106 to adjust the light or image collection functions to the desired levels. In this way, light control is automatic and transparent to the user and adds no additional time to system operation. Similarly, fluorescent excitation illumination controller 102 is used in conjunction with the camera and image collection adjustments to compensate for the variations in fluorescence in various samples. The light control software samples the output from the camera at intervals (such as between loading of slide carriers and may include sampling during image collection), and commands the fluorescent excitation illumination controller 102 to adjust the fluorescent excitation light or image exposure time to a desired level. In addition, the fluorescent excitation illumination controller 102 may control the filter wheel or wavelength 47. The system processor 23 is a high performance processor of at least 200 MHz, for example, the system processor may comprise dual parallel, Intel, 1 GHZ devices. Advances in processors are being routinely made in the computer industry. Accordingly, the disclosure should not be limited by the type of processor or speed of the processor disclosed herein.

Figure 4:
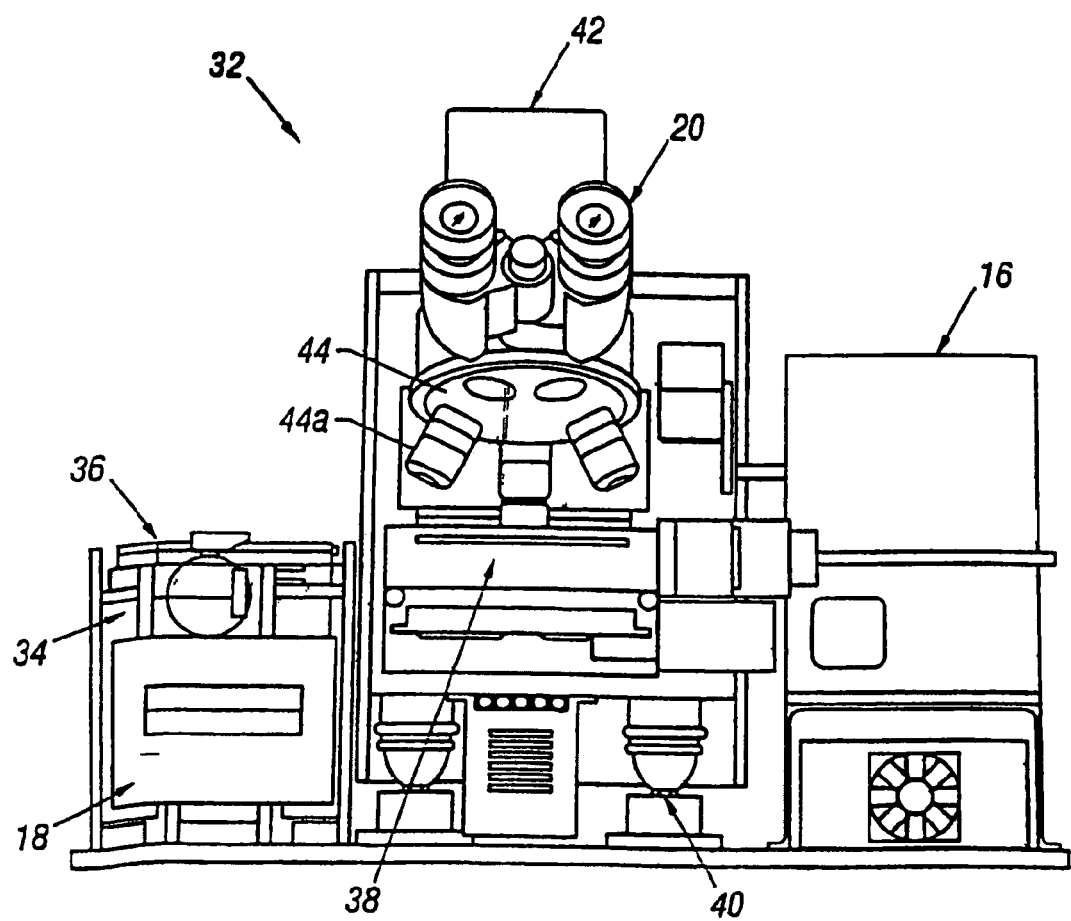
FIG. 4 is a plan view of the apparatus of FIG. 1 having the housing removed.
Figure 5:
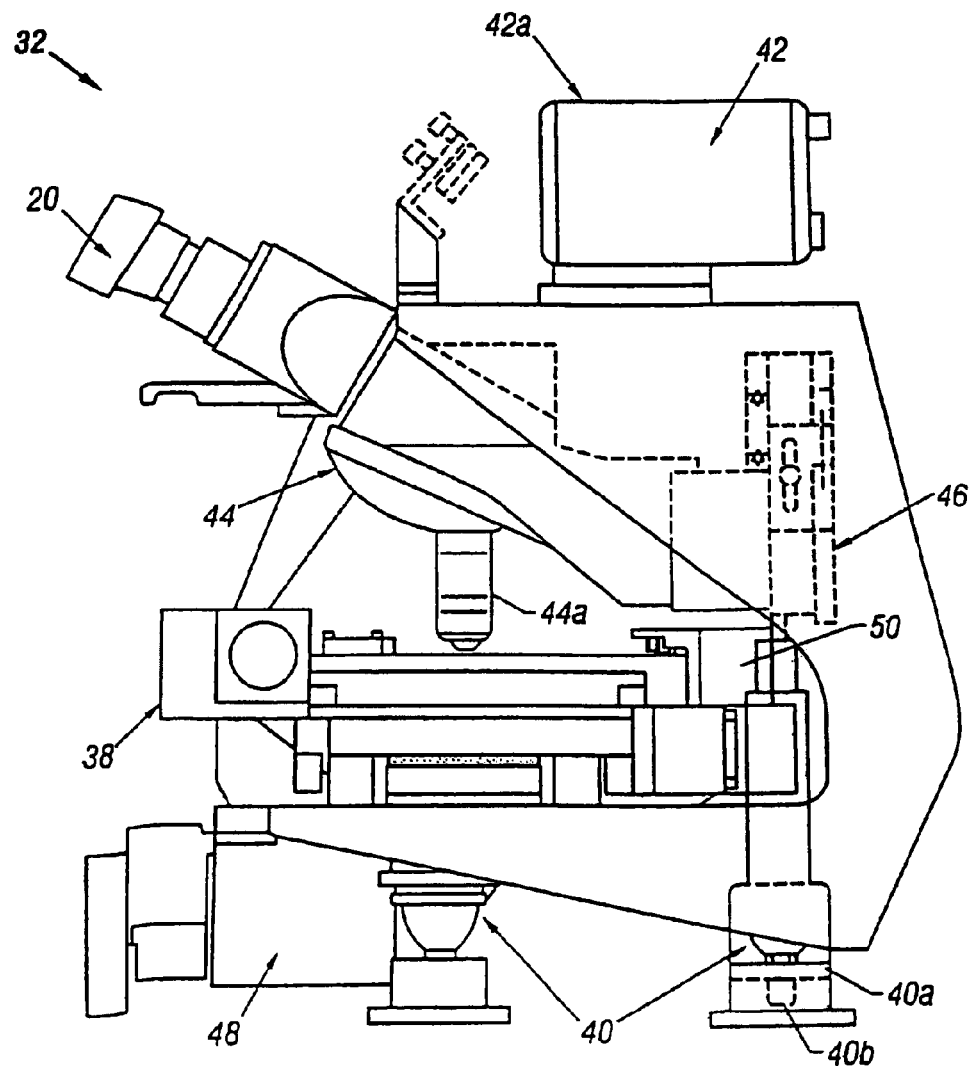
FIG. 5 is a side view of a microscope subsystem of the apparatus of FIG. 1.

Referring now to FIGS. 4 and 5, further detail of the apparatus 10 is shown. FIG. 4 shows a plan view of the apparatus 10 with the housing 12 removed. Shown is slide carrier unloading assembly 34 and unloading platform 36 which in conjunction with slide carrier output hopper 18 function to receive slide carriers which have been analyzed. Vibration isolation mounts 40, shown in further detail in FIG. 5, am provided to isolate the microscope subsystem 32 from mechanical shock and vibration that can occur in a typical laboratory environment. In addition to external sources of vibration, the high-speed operation of the X-Y stage 38 can induce vibration into the microscope subsystem 32. Such sources of vibration can be isolated from the electro-optical subsystems to avoid any undesirable effects on image quality. The isolation mounts 40 comprise a spring 40*a* and piston 40*b* (see FIG. 5) submerged in a high viscosity silicon gel which is enclosed in an elastomer membrane bonded to a casing to achieve damping factors on the order of about 17 to 20%. Other dampening devices are known in the art and may be substituted or combined with the dampening device provided herein. Occulars 20 are shown in FIGS. 4 and 5, however, their presence is an optional feature. The occulars 20 may be absent without departing from the advantages or functionality of the system.

Figure 6:
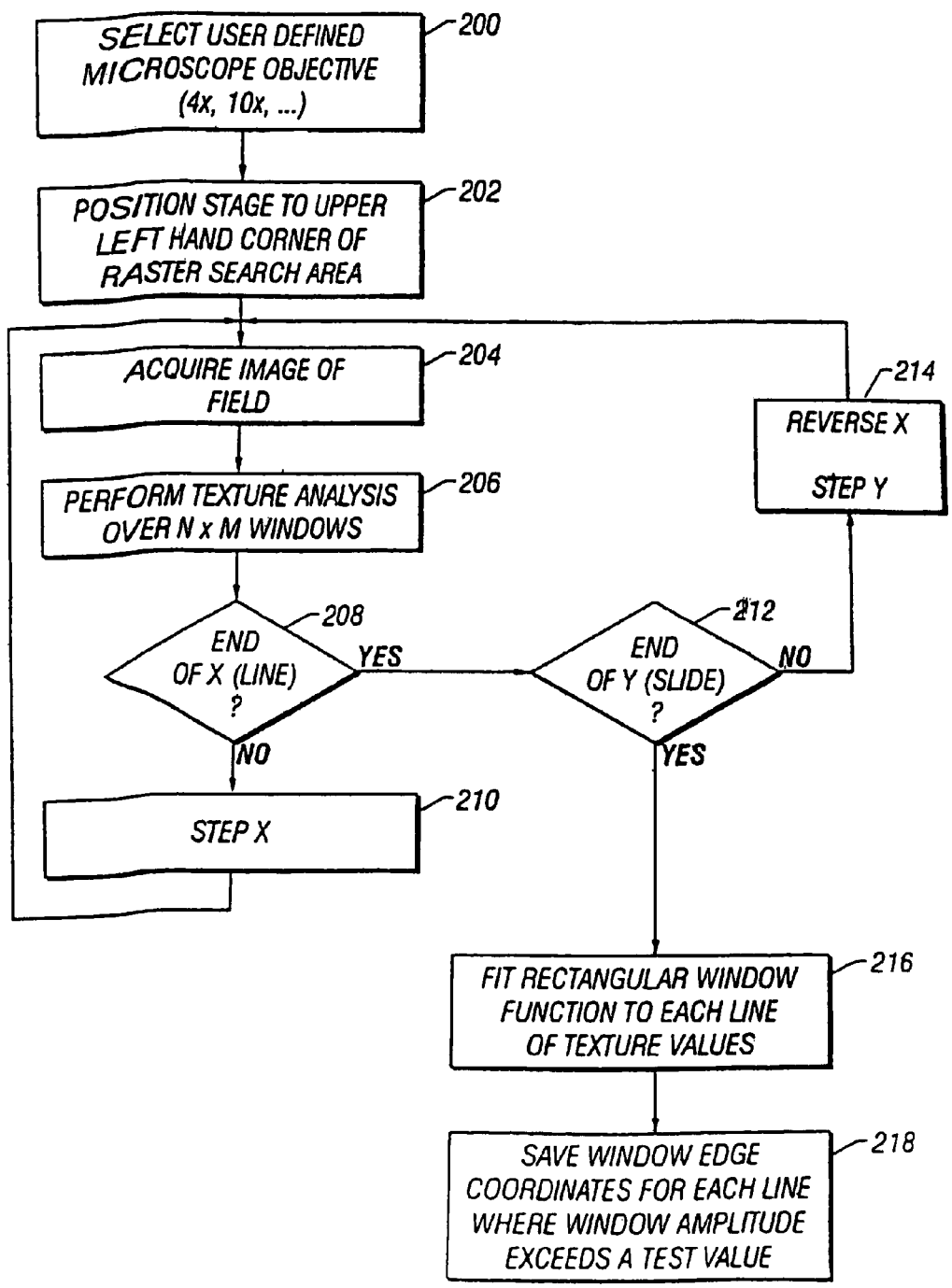
FIG. 6 is a flow diagram of the procedure for automatically determining a scan area.
Figure 7:
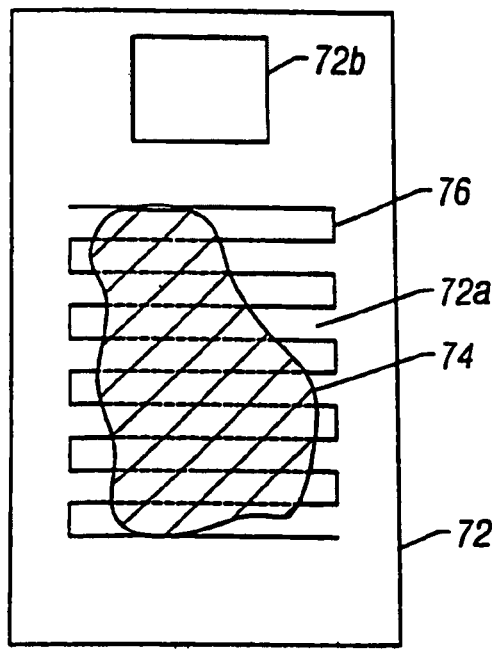
FIG. 7 shows the scan path on a prepared slide in the procedure of FIG. 6.

One feature of the disclosure automatically determines the scan area using a texture or density analysis process. FIG. 6 is a flow diagram that describes the processing associated with the automatic location of a scan area. As shown in this flow diagram, a basic method is to pre-scan the entire slide area under transmitted light to determine texture features that indicate the presence of a smear or tissue and to discriminate these areas from dirt and other artifacts. In addition, one or more distinctive features may be identified and the coordinates determined in order to make corrections to identify objects of interest in a serial subsample as described herein and using techniques known in the art.

Figure 8:
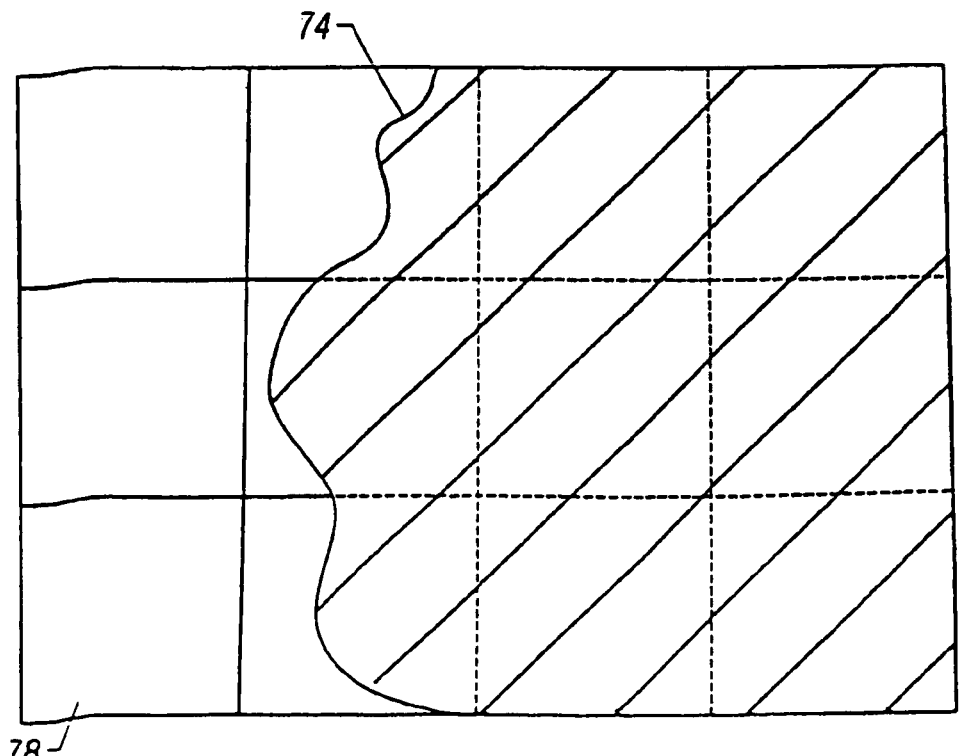
FIG. 8 illustrates an image of a field acquired in the procedure of FIG. 6.

As a first step the system determines whether a user defined microscope objective has been identified 200. The system then sets the stage comprising the sample to be scanned at a predetermined position, such as the upper left hand corner of a raster search area 202. At each location of a raster scan, an image such as in FIG. 8 is acquired 204 and analyzed for texture/border information 206. Since it is desired to locate the edges of the smear or tissue sample within a given image, texture analyses are conducted over areas called windows 78 (FIG. 8), which are smaller than the entire image as shown in FIG. 8. The process iterates the scan across the slide at steps 208, 210, 212, and 214.

The texture analysis process can be performed at a lower magnification, such as at a 4× objective, for a rapid analysis. One reason to operate at low magnification is to image the largest slide area at any one time. Since cells do not yet need to be resolved at this stage of the overall image analysis, the 4× magnification works well. Alternatively, a higher magnification scan can be performed, which may take additional time due to the field of view being smaller and requiring additional images to be processed. On a typical slide, a portion of the end of the slide is reserved for labeling with identification information. Excepting this label area, the entire slide is scanned in a raster scan fashion to yield a number of adjacent images (the images can be displayed on a computer display to provide a "reconstructed" image comprising adjacent images associated with one another). Texture values for each window include the pixel variance over a window, the difference between the largest and smallest pixel value within a window, and other indicators. The presence of a smear or tissue raises the texture values compared with a blank area.

To accommodate non-uniformity of a tissue, texture analysis provides a texture value for each analyzed area. The texture value tends to gradually rise as the scan proceeds across a smear tissue from a thin area to a thick area, reaches a peak, and then falls off again to a lower value as a thin area at the edge is reached. The problem is then to decide from the series of texture values the beginning and ending, or the edges, of the smear or tissue. The texture values are fit to a square wave waveform since the texture data does not have sharp beginnings and endings.

After conducting this scanning and texture evaluation operation, one must determine which areas of elevated texture values represent the desired smear or tissue, and which represent undesired artifacts. This is accomplished by fitting a step function, on a line-by-line basis, to the texture values. This function, which resembles a single square wave beginning at one edge and ending at the other edge and having an amplitude, provides the means for discrimination. The amplitude of the best-fit step function is utilized to determine whether smear (tissue) or dirt is present since relatively high values indicate smear (tissue). If it is decided that smear (tissue) is present, the beginning and ending coordinates of this pattern are noted until all lines have been processed, and the smear (tissue) sample area.

The first pass scan above can be used to determine a particular orientation of a sample. For example, digital images are comprised of a series of pixels arranged in a matrix, a grayscale value is can be attributed to each pixel to indicate the appearance thereof of the image. "Orientation matching" between two samples (e.g., two serial sections stained with different agents) is then performed by comparing these grayscale values relative to their positions in both the first sample image (i.e., the template) and the second sample image. A match is found when the same or similar pattern is found in the second image when compared to the first image. Such systems are typically implemented in a computer for use in various manufacturing and robotic applications and are applicable to the methods and systems of the disclosure. For example, such systems have been utilized to automate tasks such as semiconductor wafer handling operations, fiducial recognition for pick-and-place printed circuit board (PCB) assembly, machine vision for quantification or system control to assist in location of objects on conveyor belts, pellets, and trays, and automated recognition of printed matter to be inspected, such as alignment marks. The matrix of pixels used to represent such digital images are typically arranged in a Cartesian coordinate system or other arrangement of non-rectangular pixels, such as hexagonal or diamond shaped pixels. Recognition methods usually require scanning the search image scene pixel by pixel in comparison with the template, which is sought. Further, known search techniques allow for transformations such as rotation and scaling of the template image within the second sample image, therefore requiring the recognition method to accommodate for such transformations.

Normalized grayscale correlation (NOC) has been used to match digital images reliably and accurately, as is disclosed in U.S. Pat. No. 5,602,937, entitled "Methods and Apparatus for Machine Vision High Accuracy Searching," assigned to Cognex Corporation. In addition, such software is available commercially through the Matrox Imaging Library version 7.5 (Matrox Electronic Systems Ltd., Canada).

After an initial focusing operation described further herein, the scan area of interest is scanned to acquire images for image analysis. In one aspect, a bar code or computer readable label placed on the slide comprises instructions regarding the processing parameters of a particular slide as well as additional information such as a subject's name/initials or other identification. Depending upon the type of scan to be performed (e.g., fluorescence and/or transmitted light) a single low magnification image or a complete scan of the slide at low magnification is made to identify and locate candidate objects of interest, followed by further image analysis of the candidate objects of interest at high magnification in order to confirm the candidate cells or objects or area of interest. An alternate method of operation is to perform high magnification image analysis of each candidate object of interest immediately after the object has been identified at low magnification. The low magnification scanning then resumes, searching for additional candidate objects of interest. Since it takes on the order of a few seconds to change objectives, this alternate method of operation would take longer to complete.

To identify structure in tissue that cannot be captured in a single field of view image or a single staining/labeling technique, the disclosure provides a method for histological reconstruction to analyze many fields of view on potentially many slides simultaneously. The method couples composite images in an automated manner for processing and analysis. A slide on which is mounted a cellular specimen stained to identify objects of interest is supported on a motorized stage. An image of the cellular specimen is generated, digitized, and stored in memory. As the viewing field of the objective lens is smaller than the entire cellular specimen, a histological reconstruction is made. These stored images of the entire tissue section may then be placed together in an order such that the sample is reconstructed.

An overall detection process for a candidate cell or object of interest includes a combination of decisions made at both a low (e.g., 4× or 10×) and a high magnification (e.g., 40×) level. Decision-making at the low magnification level is broader in scope, e.g., objects that loosely fit the relevant color, size, and shape characteristics are identified at a 4× or 10× level.

Analysis at the 40× magnification level then proceeds to refine the decision-making and confirm objects as likely cells or candidate objects of interest. For example, at the 40× level it is not uncommon to find that some objects that were identified at 4× or 10× are artifacts, which the analysis process will then reject. In addition, closely packed objects of interest appearing at 4× or 10× are separated at the 40× level. In a situation where a cell straddles or overlaps adjacent image fields, image analysis of the individual adjacent image fields could result in the cell being rejected or undetected. To avoid missing such cells, the scanning operation compensates by overlapping adjacent image fields in both the x and y directions. An overlap amount greater than half the diameter of an average cell is desirable. In one embodiment, the overlap is specified as a percentage of the image field in the x and y directions. Alternatively, a reconstruction method as described above may be used to reconstruct the image from multiple fields of view. The reconstructed image is then analyzed and processed to find objects or areas of interest.

The time to complete an image analysis can vary depending upon the size of the scan area and the number of candidate cells or objects or area of interest identified. For example, in one embodiment, a complete image analysis of a scan area of two square centimeters in which 50 objects of interest are confirmed can be performed in about 12 to 15 minutes. This example includes not only focusing, scanning and image analysis but also the saving of 40× images as a mosaic on hard drive 21 (FIG. 2).

However the scan area is defined, an initial focusing operation should be performed on each slide prior to scanning. This is required since slides differ, in general, in their placement in a carrier. These differences include slight variations of tilt of the slide in its carrier. Since each slide must remain in focus during scanning, the degree of tilt of each slide must be determined. This is accomplished with an initial focusing operation that determines the exact degree of tilt, so that focus can be maintained automatically during scanning.

The methods may vary from simple to more complex methods involving IR beam reflection and mechanical gauges. The initial focusing operation and other focusing operations to be described later utilize a focusing method based on processing of images acquired by the system. This method results in lower system cost and improved reliability since no additional parts need be included to perform focusing. The basic method relies on the fact that the pixel value variance (or standard deviation) taken about the pixel value mean is maximum at best focus. A "brute-force" method could simply step through focus, using the computer controlled Z, or focus stage, calculate the pixel variance at each step, and return to the focus position providing the maximum variance. Such a method is time consuming. One method includes the determination of pixel variance at a relatively coarse number of focal positions, and then the fitting a curve to the data to provide a faster means of determining optimal focus. This basic process is applied in two steps, coarse and fine.

During a coarse focusing step, the z stage is stepped over a user-specified range of focus positions, with step sizes that are also user-specified. It has been found that for coarse focusing, these data are a close fit to a Gaussian function. Therefore, this initial set of variance versus focus position data are least-squares fit to a Gaussian function. The location of the peak of this Gaussian curve determines the initial or coarse estimate of focus position.

Following this, a second stepping operation is performed utilizing smaller steps over a smaller focus range centered on the coarse focus position. Experience indicates that data taken over this smaller range are generally best fit by a second order polynomial. Once this least squares fit is performed at the peak of the second order curve provides the fine focus position.

After determination of the best-fit focus plane, the scan area is scanned in an X raster scan over the scan area as described earlier. During scanning, the X stage is positioned to the starting point of the scan area, the focus (Z) stage is positioned to the best fit focus plane, an image is acquired and processed as described herein, and this process is repeated for all points over the scan area. In this way, focus is maintained automatically without the need for time-consuming refocusing at points during scanning. Prior to confirmation of candidate cells or objects or areas of interest at a 40× or 60× level, a refocusing operation is conducted since the use of this higher magnification requires more precise focus than the best-fit plane provides. This process is similar to the fine focus method described earlier in that the object is to maximize the image pixel variance. This is accomplished by stepping through a range of focus positions with the z stage, calculating the image variance at each position, fitting a second order polynomial to these data, and calculating the peak of this curve to yield an estimate of the best focus position. This final focusing step differs from previous ones in that the focus range and focus step sizes are smaller since this magnification requires focus settings to within 0.5 micron or better. It should be noted that for some combinations of cell staining characteristics, improved focus can be obtained by numerically selecting the focus position that provides the largest variance, as opposed to selecting the peak of the polynomial. In such cases, the polynomial is used to provide an estimate of best focus, and a final step selects the actual Z position giving highest pixel variance. It should also be noted that if at any time during the focusing process at 40× or 60× the parameters indicate that the focus position is inadequate, the system automatically reverts to a coarse focusing process as described above. This ensures that variations in specimen thickness can be accommodated in an expeditious manner. For some biological samples and stains, the focusing methods discussed above do not provide optimal focused results. For example, certain white blood cells known as neutrophils may be stained with Fast Red, a commonly known stain, to identify alkaline phosphatase in the cytoplasm of the cells. To further identify these cells and the material within them, the specimen may be counterstained with hematoxylin to identify the nucleus of the cells. In cells so treated, the cytoplasm bearing alkaline phosphatase becomes a shade of red proportionate to the amount of alkaline phosphatase in the cytoplasm and the nucleus becomes blue. However, where the cytoplasm and nucleus overlap, the cell appears purple. Where a sample has been labeled with a fluorescent agent the focus plane may be based upon the intensity of a fluorescent signal. For example, as the image scans through a Z-plane of the sample, the intensity of fluorescence will change as the focus plane passes closer to the fluorescence indicator.

In an effort to find a best focal position at high magnification, a focus method, begins by selecting a pixel near the center of a candidate object of interest and defining a region of interest centered about the selected pixel. Typically, the width of the region of interest is a number of columns, which is a power of 2. This width determination arises from subsequent processing of the region of interest using a one dimensional Fast Fourier Transform (FFT) technique. As is well known in the art, processing columns of pixel values using the FFT technique is facilitated by making the number of columns to be processed a power of two. While the height of the region of interest is also a power of two, it need not be unless a two dimensional FFT technique is used to process the region of interest.

After the region of interest is selected, the columns of pixel values are processed using a one dimensional FFT to determine a spectra of frequency components for the region of interest. The frequency spectra ranges from DC to some highest frequency component. For each frequency component, a complex magnitude is computed. The complex magnitudes for the frequency components, which range from approximately 25% of the highest component to approximately 75% of the highest component, are squared and summed to determine the total power for the region of interest. Alternatively, the region of interest may be processed with a smoothing window, such as a Hanning window, to reduce the spurious high frequency components generated by the PFT processing of the pixel values in the region of interest. Such preprocessing of the region of interest permits complex magnitudes over the complete frequency range to be squared and summed. After the power for a region has been computed and stored 256, a new focal position is selected, focus adjusted 258 and 260, and the process repeated. After each focal position has been evaluated, the one having the greatest power factor is selected as the one best in focus.

The following describes the image processing methods which are utilized to decide whether a candidate object of interest such as a stained tumor cell is present in a given image, or field, during the scanning process. Candidate objects of interest, which are detected during scanning, are reimaged at higher (40× or 60×) magnification, the decision confirmed, and an image of the object of interest as well as its coordinates saved for later review. In one aspect of the disclosure, objects of interest are first acquired and identified under transmitted light.

Figure 9:
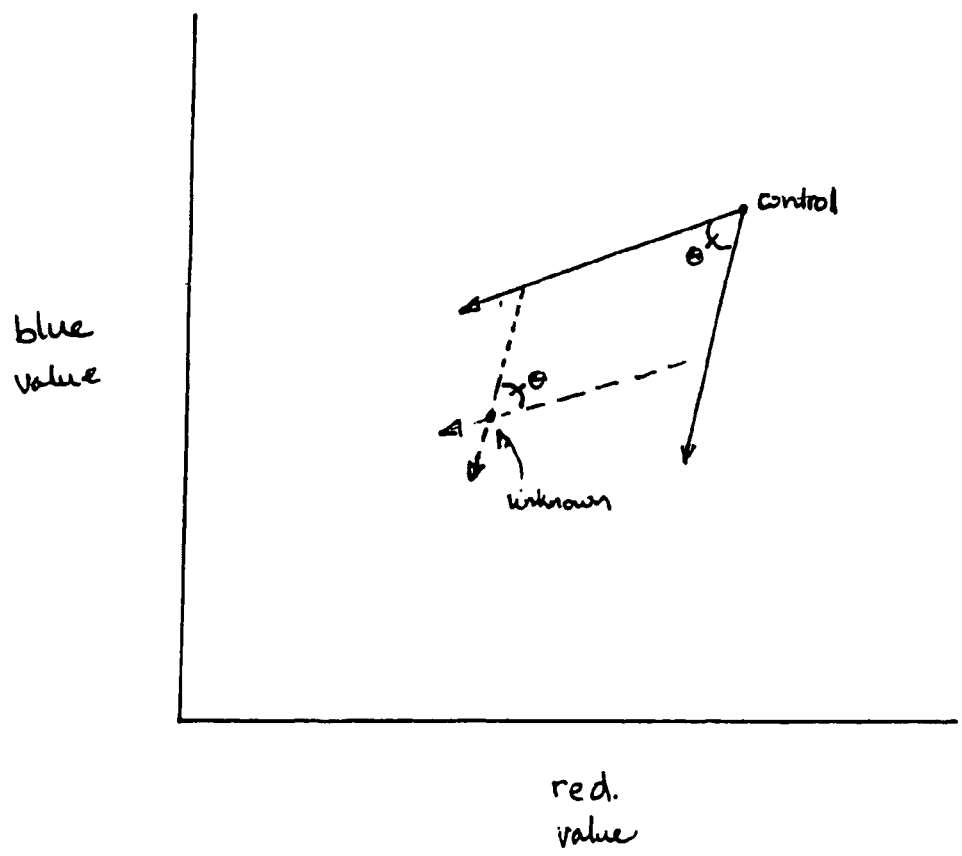
FIG. 9 is a graph showing a method of the disclosure.
Figure 10:
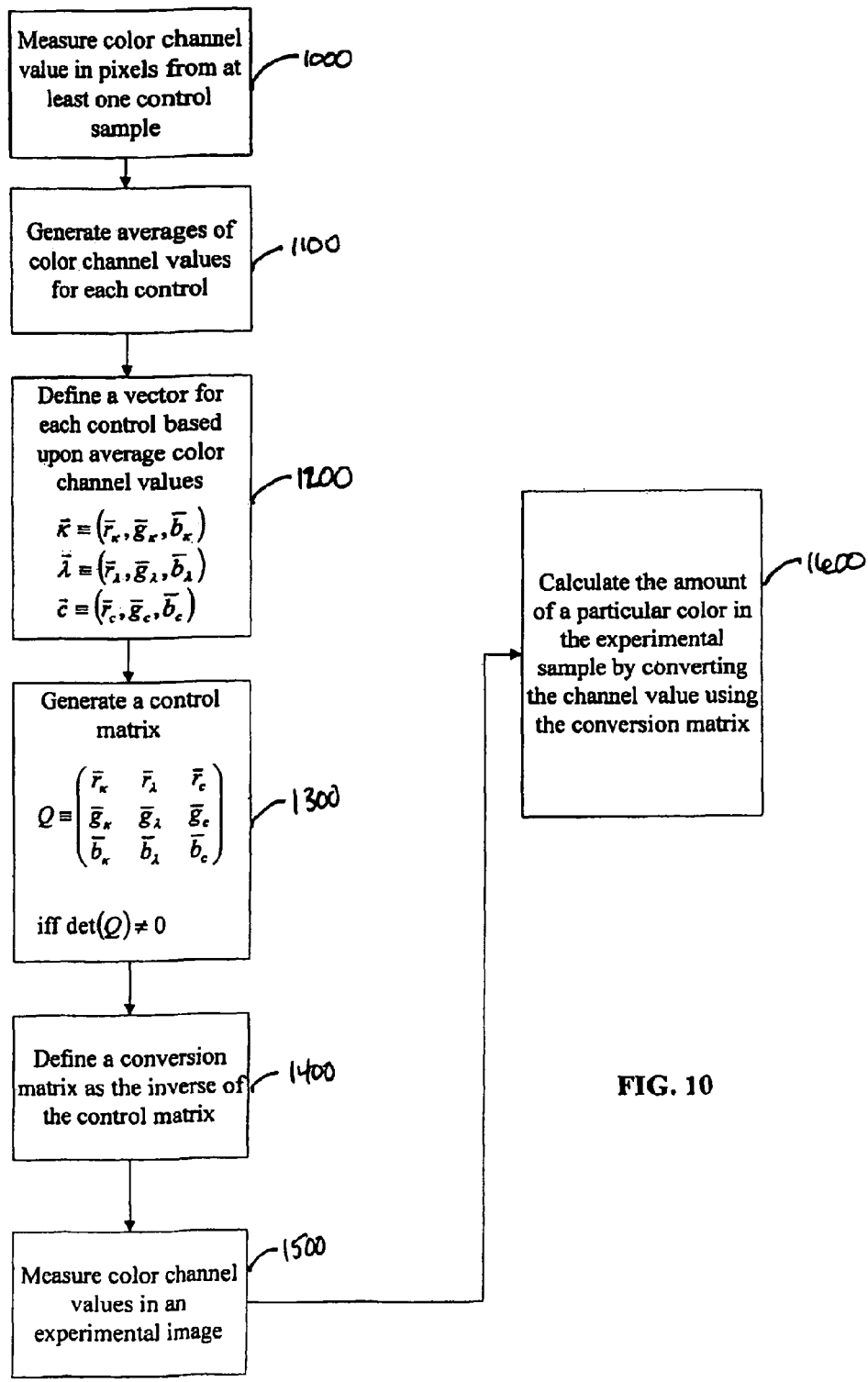
FIG. 10 shows a process of the disclosure for identifying the amount of a particular color or stain in a sample comprising a plurality of colors or stains.

During such acquisition, an algorithm of the disclosure is use to quantify a color in a sample comprising multiple colors. Typically a series of control slides (e.g., 2 or more control slides) comprising a single color (e.g., a single stain rendering a color precipitate) will be imaged by the system (see, FIG. 10 at 1000). A measure of a color channel value in a plurality of pixels comprising a single color of interest is made (1000). This information defines a vector for each of the plurality of control samples, wherein each vector comprises an average of each color channel value present in the control (an example of such vectors are shown in FIG. 9; see also FIG. 10 at 1200). This information is then used to define a control matrix comprising each of the averages for each of the color channels (1300). A conversion matrix is then generated comprising the inverse of the control matrix (1400). Once the control measurements are made, the system then measures color channel values in an image of an experimental sample comprising a plurality of colors of interest (1500), each of the pixels comprising a plurality of color channels. The amount of a particular color in the experimental sample can then be calculated by converting the channel values in the experimental sample using the conversion matrix (1600). The disclosure uses the Red, Green, Blue (RGB), in the specific examples, however one of skill in the art will recognize that various other colors and color space may be used in the methods of the disclosure. It will also be recognized that the number of colors in the experimental sample can be less than or equal to the number of color channels measure in the controls. The methods of the disclosure may be combined with additional imaging algorithms and processes to identify objects or areas of interest in a sample. Such imaging process may be performed prior to, concurrently with, or after the exemplary process set forth in FIG. 10.

Additional imaging processes includes color space conversion, low pass filtering, background suppression, artifact suppression, morphological processing, and blob analysis. One or more of these steps can optionally be eliminated. The operator may optionally configure the system to perform any or all of these steps and whether to perform certain steps more than once or several times in a row. It should also be noted that the sequence of steps may be varied and thereby optimized for specific reagents or reagent combinations. Where a sample has been stained or contacted with multiple agents that "mark" different components of a biological sample, the methods and algorithms described above can be used to determine the quantity of a particular stain at a particular location. As mentioned above, control sample may be used that have each been stained with a single type of stain. These controls can then be used to determine the amount of stain in a sample comprising a combination of the individual stains.

In the case of a sample comprising multiple markers stained with different agents, a vector of the average of r, g, and b values are made for each control slide stained with a single agent. A sample stained with multiple agents is then measured and the pixel value calculated. Each pixel channel obtained from the experimental sample will be proportional to the amount of the corresponding stain in an area of interest. A conversion factor determined from the controls is then used to directly and independently determine the amount of the multiple stains present in each pixel value.

In general, the candidate objects of interest, such as tumor cells, are detected based on a combination of characteristics, including size, shape, and color. In one aspect, a step in the detection of the candidate object of interest or area of interested is a measurement of a particular color in an image of the sample based, in part, upon the process generally described in FIG. 10.

In another aspect, The chain of decision making based on these characteristics begins with a color space conversion process. The optical sensing array coupled to the microscope subsystem outputs a color image comprising a matrix of pixels. Each pixel comprises a plurality of color channels (e.g., red, green, and blue (RGB)) signal values.

Samples are generally stained with one or more standard stains (e.g., DAB, New Fuchsin, AEC), which are "reddish" in color. Candidate objects of interest retain more of the stain and thus appear red while normal cells remain unstained. The specimens may also be counterstained with hematoxylin so the nuclei of normal cells or cells not containing an object of interest appear blue. In addition to these objects, dirt and debris can appear as black, gray, or can also be lightly stained red or blue depending on the staining procedures utilized. The residual plasma or other fluids also present on a smear (tissue) may also possess some color.

In one aspect of the disclosure, a color conversion operation includes forming a ratio of two of the RGB signal values to provide a means for discriminating color information. With three signal values for each pixel, nine different ratios can be formed: R/R, R/G, R/B, G/G, G/B, G/R, B/B, B/G, B/R. The optimal ratio to select depends upon the range of color information expected in the slide sample. As noted above, typical stains used in light microscopy for detecting candidate objects of interest such as tumor cells are predominantly red, as opposed to predominantly green or blue. Thus, the pixels of an object of interest that has been stained would contain a red component, which is larger than either the green or blue components. A ratio of red divided by blue (R/B) provides a value which is greater than one for, e.g. tumor cells, but is approximately one for any clear or white areas on the slide. Since other components of the sample, for example, normal cells, typically are stained blue, the R/B ratio for pixels of these other components (e.g., normal cells) yields values of less than one. The R/B ratio is used for separating the color information typical in these applications.

An extension of this method is also included in the disclosure. For example, 2 stains one of which marks the target molecule and another reference stain which marks all cells of the specified type (regardless of whether they have the target molecule) is used on a sample. A ratio between the target molecule and the cell marker is used in medical diagnosis. The ratio is calculated even if the target molecule is found in one sub cellular compartment and the reference marker for identifying cells of the specified type is found in another sub cellular compartment. Thus, let:

$N_p$=# of positive cells
$N_r$=total # of cells of specified type (i.e. all cells labeled in the reference compartment)
$a_p$=Average area of compartment labeled in positive cells
$a_r$=Average area of reference compartment labeled in all cells of the specified type
$P_p$=Number of pixels of positive color (labeling target molecule)
$P_r$=Number of pixels of reference color (labeling cells of the specified type)
Using the above definitions one can calculate the desired ratio:

$$R = \frac{N_p}{N_r}$$

As follows:

$$N_p = \frac{P_p}{a_p}$$

$$N_r = \frac{P_r}{a_r}$$

$$R = \frac{N_p}{N_r} = \frac{P_p a_r}{P_r a_p}$$

$$R^c = \frac{P_p^c a_r}{P_r^c a_p}$$

Where the superscript $^c$ indicates the corresponding value when measuring a control area with a known ratio.

$$\frac{a_r}{a_p} = R^c \frac{P_r^c}{P_p^c}$$

$$\therefore R = \frac{P_p R^c P_r^c}{P_r P_p^c}$$

This shows that if an area with known ratio of positive to specified type cells is known one can determine the ratio in another area from the ratios of stained pixels. This is true even if the positive cells are being recognized on the basis of a stain that marks a different compartment than the stain that marks all cells of the specified type.

Other methods exist for discriminating color information. One method converts the RGB color information into another color space, such as HSI (hue, saturation, intensity) space. In such a space, distinctly different hues such as red, blue, green, yellow, may be readily separated. In addition, relatively lightly stained objects may be distinguished from more intensely stained ones by virtue of differing saturations. Methods of converting from RGB space to HSI space are described in U.S. Pat. No. 6,404,916 B1, the entire contents of which are incorporated by reference. In brief, color signal inputs are received by a converter that converts the representation of a pixel's color from red, green, and blue (RGB) signals to hue, saturation, and intensity signals (HSI). The conversion of RGB signals to HSI signals is equivalent to a transformation from the rectilinear RGB coordinate system used in color space to a cylindrical coordinate system in which hue is the polar coordinate, saturation is the radial coordinate, and intensity is the axial coordinate, whose axis lies on a line between black and white in coordinate space. A number of algorithms to perform this conversion are known, and computer chips are available to perform the algorithms.

Exemplary methods include a process whereby a signal representative of a pixel color value is converted to a plurality of signals, each signal representative of a component color value including a hue value, a saturation value, and an intensity value. For each component color value, an associated range of values is set. The ranges together define a non-rectangular subvolume in HSI color space. A determination is made whether each of the component values falls within the associated range of values. The signal is then outputting, indicating whether the pixel color value falls within the color range in response to each of the component values falling within the associated range of values. The range of values associated with the hue value comprises a range of values between a high hue value and a low hue value, the range of values associated with the saturation value comprises a range of values above a low saturation value, and the range of values associated with the intensity value comprises a range of values between a high intensity value and a low intensity value.

Such methods can be executed on an apparatus that may include a converter to convert a signal representative of a pixel color value to a plurality of signals representative of component color values including a hue value, a saturation value, and an intensity value. The hue comparator determines if the hue value falls within a first range of values. The apparatus may further include a saturation comparator to determine if the saturation value falls within a second range of values, as well as an intensity comparator to determine if the intensity value falls within a third range of values. In addition, a color identifier connected to each of the hue comparator, the saturation comparator, and the intensity comparator, is adapted to output a signal representative of a selected color range in response to the hue value falling within the first range of values, the saturation value falling within the second range of values, and the intensity value falling within the third range of values. The first range of values, the second range of values, and the third range of values define a non-rectangular subvolume in HSI color space, wherein the first range of values comprises a plurality of values between a low hue reference value and a high hue reference value, the second range of values comprises a plurality of values above a low saturation value, and the third range of values comprises a plurality of values between a low intensity value and a high intensity value.

In yet another approach, one could obtain color information by taking a single color channel from the optical sensing array. As an example, consider a blue channel, in which objects that are red are relatively dark. Objects that are blue, or white, are relatively light in the blue channel. In principle, one could take a single color channel, and simply set a threshold wherein everything darker than some threshold is categorized as a candidate object of interest, for example, a tumor cell, because it is red and hence dark in the channel being reviewed. However, one problem with the single channel approach occurs where illumination is not uniform. Non-uniformity of illumination results in non-uniformity across the pixel values in any color channel, for example, tending to peak in the middle of the image and dropping off at the edges where the illumination falls off. Performing thresholding on this non-uniform color information runs into problems, as the edges sometimes fall below the threshold, and therefore it becomes more difficult to pick the appropriate threshold level. However, with the ratio technique, if the values of the red channel fall off from center to edge, then the values of the blue channel also fall off center to edge, resulting in a uniform ratio at non-uniform lighting. Thus, the ratio technique is more immune to illumination.

As described, the color conversion scheme is relatively insensitive to changes in color balance, e.g., the relative outputs of the red, green, and blue channels. However, some control is necessary to avoid camera saturation, or inadequate exposures in any one of the color bands. This color balancing is performed automatically by utilizing a calibration slide consisting of a clear area, and a "dark" area having a known optical transmission or density. The system obtains images from the clear and "dark" areas, calculates "white" and "black" adjustments for the image-frame grabber or image processor 25, and thereby provides correct color balance.

In addition to the color balance control, certain mechanical alignments am automated in this process. The center point in the field of view for the various microscope objectives as measured on the slide can vary by several (or several tens of) microns. This is the result of slight variations in position of the microscope objectives 44a as determined by the turret 44 (FIGS. 2 and 4), small variations in alignment of the objectives with respect to the system optical axis, and other factors. Since it is desired that each microscope objective be centered at the same point, these mechanical offsets must be measured and automatically compensated.

This is accomplished by imaging a test slide that contains a recognizable feature or mark. An image of this pattern is obtained by the system with a given objective, and the position of the mark determined. The system then rotates the turret to the next lens objective, obtains an image of the test object, and its position is redetermined. Apparent changes in position of the test mark are recorded for this objective. This process is continued for all objectives. Once these spatial offsets have been determined, they are automatically compensated for by moving the XY stage 38 by an equal (but opposite) amount of offset during changes in objective. In this way, as different lens objectives are selected, there is no apparent shift in center point or area viewed. A low pass filtering process precedes thresholding. An objective of thresholding is to obtain a pixel image matrix having only candidate cells or objects of interest, such as tumor cells above a threshold level and everything else below it. However, an actual acquired image will contain noise. The noise can take several forms, including white noise and artifacts. The microscope slide can have small fragments of debris that pick up color in the staining process and these are known as artifacts. These artifacts are generally small and scattered areas, on the order of a few pixels, which are above the threshold. The purpose of low pass filtering is to essentially blur or smear the entire color converted image. The low pass filtering process will smear artifacts more than larger objects of interest, such as tumor cells and thereby eliminate or reduce the number of artifacts that pass the thresholding process. The result is a cleaner thresholded image downstream. In the low pass filter process, a 3×3 matrix of coefficients is applied to each pixel in the x-image. A preferred coefficient matrix is as follows:

| 1/9 | 1/9 | 1/9 |
| --- | --- | --- |
| 1/9 | 1/9 | 1/9 |
| 1/9 | 1/9 | 1/9 |

At each pixel location, a 3×3 matrix comprising the pixel of interest and its neighbors is multiplied by the coefficient matrix and summed to yield a single value for the pixel of interest. The output of this spatial convolution process is again a pixel matrix. As an example, consider a case where the center pixel and only the center pixel, has a value of 255 and each of its other neighbors, top left, top, top right and so forth, have values of 0.

This singular white pixel case corresponds to a small object. The result of the matrix multiplication and addition using the coefficient matrix is a value of (1/9)*255 or 28.3 for the center pixel, a value which is below the nominal threshold of 128. Now consider another case in which all the pixels have a value of 255 corresponding to a large object. Performing the low pass filtering operation on a 3×3 matrix for this case yields a value of 255 for the center pixel. Thus, large objects retain their values while small objects are reduced in amplitude or eliminated. In the preferred method of operation, the low pass filtering process is performed on the X image twice in succession.

In order to separate objects of interest, such as a tumor cell in the x image from other objects and background, a thresholding operation is performed designed to set pixels within candidate cells or objects of interest to a value of 255, and all other areas to 0. Thresholding ideally yields an image in which cells of interest are white and the remainder of the image is black. A problem one faces in thresholding is where to set the threshold level. One cannot simply assume that cells of interest are indicated by any pixel value above the nominal threshold of 128. A typical imaging system may use an incandescent halogen light bulb as a light source. As the bulb ages, the relative amounts of red and blue output can change. The tendency as the bulb ages is for the blue to drop off more than the red and the green. To accommodate for this light source variation over time, a dynamic thresholding process is used whereby the threshold is adjusted dynamically for each acquired image. Thus, for each image, a single threshold value is derived specific to that image. As shown in FIG. 18, the basic method is to calculate, for each field, the mean X value, and the standard deviation about this mean 312. The threshold is then set at 314 to the mean plus an amount defined by the product of a factor (e.g., a user specified factor) and the standard deviation of the color converted pixel values. The standard deviation correlates to the structure and number of objects in the image. Typically, a user specified factor is in the range of approximately 1.5 to 2.5. The factor is selected to be in the lower end of the range for slides in which the stain has primarily remained within cell boundaries and the factor is selected to be in the upper end of the range for slides in which the stain is pervasively present throughout the slide. In this way, as areas are encountered on the slide with greater or lower background intensities, the threshold may be raised or lowered to help reduce background objects. With this method, the threshold changes in step with the aging of the light source such that the effects of the aging are canceled out. The image matrix resulting at 316 from the thresholding step is a binary image of black (0) and white (255) pixels. As is often the case with thresholding operations such as that described above, some undesired areas will lie above the threshold value due to noise, small stained cell fragments, and other artifacts. It is desired and possible to eliminate these artifacts by virtue of their small size compared with legitimate cells of interest. In one aspect, morphological processes are utilized to perform this function.

Morphological processing is similar to the low pass filter convolution process described earlier except that it is applied to a binary image. Similar to spatial convolution, the morphological process traverses an input image matrix, pixel by pixel, and places the processed pixels in an output matrix. Rather than calculating a weighted sum of the neighboring pixels as in the low pass convolution process, the morphological process uses set theory operations to combine neighboring pixels in a nonlinear fashion.

Erosion is a process whereby a single pixel layer is taken away from the edge of an object. Dilation is the opposite process, which adds a single pixel layer to the edges of an object. The power of morphological processing is that it provides for further discrimination to eliminate small objects that have survived the thresholding process and yet are not likely objects of interest (e.g., tumor cells). The erosion and dilation processes that make up a morphological "open" operation make small objects disappear yet allow large objects to remain. Morphological processing of binary images is described in detail in "Digital Image Processing", pages 127-137, G. A. Baxes, John Wiley & Sons, (1994).

Once imaging has been performed in transmitted light imaging in fluorescent light may be performed using a process described above. For example, at the completion of scanning and imaging at a higher magnification under transmitted light, the system switches from transmitted light to fluorescent excitation light and obtains images at a desired magnification objective (e.g., 40×), and each candidate cell or object of interest identified under transmitted light is reimaged under fluorescent light. Each fluorescent image is then processed with test parameters suitably modified for the fluorescent imaging. A fluorescent image comprising a fluorescently labeled object of interest is saved to storage device for review by a pathologist.

As with any imaging system, there is some loss of modulation transfer (e.g., contrast) due to the modulation transfer function (MTF) characteristics of the imaging optics, camera, electronics, and other components. Since it is desired to save "high quality" images of cells of interest both for pathologist review and for archival purposes, it is desired to compensate for these MTF losses. An MTF compensation (MTFC) is performed as a digital process applied to the acquired digital images. A digital filter is utilized to restore the high spatial frequency content of the images upon storage, while maintaining low noise levels. With this MTFC technology, image quality is enhanced, or restored, through the use of digital processing methods as opposed to conventional oil-immersion or other hardware based methods. MTFC is described further in "The Image Processing Handbook," pages 225 and 337, J. C. Rues, CRC Press (1995).

Particular uses of the methods and systems of the disclosure include the detection of the following specific markers. The HER2/neu marker, for example, may be detected though the use of an anti-HER2/neu staining system, such as a commercially available kit, like that provided by DAKO (Carpinteria, Calif.). A typical immunohistochemistry protocol includes: (1) prepare wash buffer solution; (2) deparaffinize and rehydrate sample or subsample; (3) perform epitope retrieval. Incubate 40 min in a 95° C. water bath. Cool slides for 20 min at room temperature; (4) apply peroxidase blocking reagent. Incubate 5 min; (5) apply primary antibody or negative control reagent. Incubate 30 min+/−1 min at room temperature. Rinse in wash solution. Place in wash solution bath; (6) apply peroxidase labeled polymer. Incubate 30 min+/−1 min at room temperature. Rinse in wash solution. Place in wash solution bath; (7) prepare DAB substrate chromagen solution; (8) apply substrate chromogen solution (DAB). Incubate 5-10 min. Rinse with distilled water; (9) counterstain; (10) mount coverslips. The slide includes a cover-slip medium to protect the sample and to introduce optical correction consistent with microscope objective requirements. A coverslip typically covers the entire prepared specimen. Mounting the coverslip does not introduce air bubbles obscuring the stained specimen. This coverslip could potentially be a mounted 1½ thickness coverslip with DAKO Ultramount medium; (11) a set of staining control slides are run with every worklist. The set includes a positive and negative control. The positive control is stained with the anti-HER2 antibody and the negative is stained with another antibody. Both slides are identified with a unique barcode. Upon reading the barcode, the instrument recognizes the slide as part of a control set, and runs the appropriate application. There may be one or two applications for the stain controls; (12) a set of instrument calibration slides includes the slides used for focus and color balance calibration; (13) a dedicated carrier is used for one-touch calibration. Upon successful completion of this calibration procedure, the instrument reports itself to be calibrated. Upon successful completion of running the standard slides, the user is able to determine whether the instrument is within standards and whether the inter-instrument and intra-Instrument repeatability of test results.

A hematoxylin/eosin (H/E) slide is prepared with a standard H/E protocol. Standard solutions include the following: (1) Gills hematoxylin (hematoxylin 6.0 g; aluminum sulphate 4.2 g; citric acid 1.4 g; sodium iodate 0.6 g; ethylene glycol 269 ml; distilled water 680 ml); (2) eosin (eosin yellowish 1.0 g; distilled water 100 ml); (3) lithium carbonate 1% (lithium carbonate 1 g; distilled water 100 g); (4) acid alcohol 1% 70% (alcohol 99 ml conc; hydrochloric acid 1 ml); and (5) Scott's tap water. In a beaker containing 1 L distilled water, add 20 g sodium bicarbonate and 3.5 g magnesium sulphate. Add a magnetic stirrer and mix thoroughly to dissolve the salts. Using a filter funnel, pour the solution into a labeled bottle.

The staining procedure is as follows: (1) bring the sections to water; (2) place sections in hematoxylin for 5 min; (3) wash in tap water; (4) 'blue' the sections in lithium carbonate or Scott's tap water, (5) wash in tap water; (6) place sections in 1% acid alcohol for a few seconds; (7) wash in tap water; (8) place sections in eosin for 5 min; (9) wash in tap water, and (10) dehydrate, clear. Mount sections. The results of the H/E staining provide cells with nuclei stained blue-black, cytoplasm stained varying shades of pink; muscle fibers stained deep pinky red; fibrin stained deep pink; and red blood cells stained orange-red.

In another aspect, the disclosure provides automated methods for analysis of estrogen receptor and progesterone receptor. The estrogen and progesterone receptors, like other steroid hormone receptors, play a role in developmental processes and maintenance of hormone responsiveness in cells. Estrogen and progesterone receptor interaction with target genes is of importance in maintenance of normal cell function and is also involved in regulation of mammary tumor cell function. The expression of progesterone receptor and estrogen receptor in breast tumors is a useful indicator for subsequent hormone therapy. An anti-estrogen receptor antibody labels epithelial cells of breast carcinomas which express estrogen receptor. An immunohistochemical assay of the estrogen receptor is performed using an anti-estrogen receptor antibody, for example the well-characterized 1D5 clone, and the methods of Pertchuk, et al. (Cancer 77: 2514-2519, 1996) or a commercially available immunohistochemistry system such as that provided by DAKO (Carpenteria Calif.; DAKO LSAB2 Immunostaining System). Accordingly, the disclosure provides a method whereby tumor cells are identified using a first agent and normal light microscopy and then further characterized using antibodies to a progesterone and/or estrogen receptor, wherein the antibodies are tagged with a fluorescent agent.

For example, the labeling of progesterone receptor has been demonstrated in the nuclei of cells from various histologic subtypes. An anti-progesterone receptor antibody labels epithelial cells of breast carcinomas which express progesterone receptor. An immunohistochemical assay of the progesterone receptor is performed using an anti-estrogen receptor antibody, for example the well-characterized 1A6 clone and methods similar to those of Pertchuk, et al. (Cancer 77: 2514-2519, 1996).

Micrometastases/metastatic recurring disease (MM/MRD). Metastasis is the biological process whereby a cancer spreads to a distant part of the body from its original site. A micrometastases is the presence of a small number of tumor cells, particularly in the lymph nodes and bone marrow. A metastatic recurring disease is similar to micrometastasis, but is detected after cancer therapy rather than before therapy. An immunohistochemical assay for MM/MRD is performed using a monoclonal antibody that reacts with an antigen (a metastatic-specific mucin) found in bladder, prostate and breast cancers. An MM/MRD can be identified by first staining cells to identify nucleic and cellular organelles or alternatively by staining cells to differentiate between bladder and other prostate cells. Subsamples corresponding to the original first subsample can then be stained with and antibody to a mucin protein, wherein the antibody is detectably labeled with a fluorescent molecule. In this way, a first subsample is prescreened to identify objects of interest including a particular cell type and then screened with a specific antibody to a molecule of interest associated with the object of interest. The first screening step allows for an automated system to identify the coordinates in a first subsample having the object of interest whereby the coordinates are then used to focus and obtaining fluorescent images in a second subsample at the same coordinates.

Another example of the application of the disclosure includes the use of MIB-1. MIB-1 is an antibody that detects the antigen Ki-67. The clinical stage at first presentation is related to the proliferative index measured with Ki-67. High index values of Ki-67 are positively correlated with metastasis, death from neoplasia, low disease-free survival rates, and low overall survival rates. For example, a first agent (e.g., a staining agent) is used to identify an object of interest such as a marker for cancer cells. A diagnosis or prognosis of a subject may then be performed by further analyzing any object of interest for the presence of Ki-67 using an antibody that is detectably labeled with a fluorescent agent. The coordinates of any such object of interest (e.g., a suspected cancer cell) are then used to focus and obtain a fluorescent image of a sample or subsample contacted with a fluorescently labeled MIB-1. The presence of a fluorescent signal at such coordinates is indicative of a correlation of the cancer cell with metastasis and/or survival rates.

In another aspect, microvessel density analysis can be performed and a determination of any cytokines, angiogenic agents, and the like, which are suspected of playing a role in the angiogenic activity identified. Angiogenesis is a characteristic of growing tumors. By identifying an angiogenic agent that is expressed or produced aberrantly compared to normal tissue, a therapeutic regimen can be identified that targets and modulates (e.g., increases or decreases) the angiogenic molecule or combination of molecules. For example, endothelial cell proliferation and migration are characteristic of angiogenesis and vasculogenesis. Endothelial cells can be identified by markers on the surface of such endothelial cells using a first agent that labels endothelial cells. An automated microscope system (such as that produced by ChromaVision Medical Systems, Inc., California) scans the sample for objects of interest (e.g., endothelial cells) stained with the first agent. The automated system then determines the coordinates of an object of interest and uses these coordinates to focus in on the sample or a subsample that has been contacted with a second fluorescently labeled agent. In one aspect, a second agent (e.g., an antibody, polypeptide, and/or oligonucleotide) that is labeled with a fluorescent indicator is then used to detect the specific expression or presence of any number of angiogenic agents.

Overexpression of the p53 oncogene has been implicated as the most common genetic alteration in the development of human malignancies. Investigations of a variety of malignancies, including neoplasms of breast, colon, ovary, lung, liver, mesenchyme, bladder and myeloid, have suggested a contributing role of p53 mutation in the development of malignancy. The highest frequency of expression has been demonstrated in tumors of the breast, colon, and ovary. A wide variety of normal cells do express a wildtype form of p53 but generally in restricted amounts. Overexpression and mutation of p53 have not been recognized in benign tumors or in normal tissue. In addition, p53 has also be implicated as a cocontributor to tumors. For example, BRCA-1 has been used as marker for ovarian cancer, however p53 has also been implicated as playing a role in BRCA-1 ovarian cancers (Rose and Buller, Minerva Ginecol. 54(3):201-9, 2002). Using the methods of the disclosure a sample is stained for BRCA-1 with a first agent and objects of interest are identified using light microscopy. The same sample or a subsample, having substantially identical coordinates with respect to an object of interest, is then contacted with a second agent comprising a fluorescent label that interacts with a p53 nucleic acid or polypeptide. The sample or subsample is then analyzed via fluorescent microscopy to identify any fluorescent signals at the coordinates associated with the object of interest to determine the presence or absence of p53 nucleic acids or polypeptides. An anti-p53 antibody useful in this embodiment includes, for example, the well-characterized DO-7 clone.

An example of an object of interest includes nucleoli, an organelle in a cell nucleus. Uses of nucleoli as objects of interest are apparent when determining cervical dysplasia. In cervical dysplasia normal or metaplastic epithelium is replaced with atypical epithelial cells that have cytologic features that are pre-malignant (nuclear hyperchromatism, nuclear enlargement and irregular outlines, increased nuclear-to-cytoplasmic ratio, increased prominence of nucleoli) and chromosomal abnormalities. The changes seen in dysplastic cells are of the same kind but of a lesser degree than those of frankly malignant cells. In addition, there are degrees of dysplasia (mild, moderate, severe).

In yet another aspect, and object of interest may be the p24 antigen of Human immunodeficiency virus (HIV). Anti-p24 antibodies are used to detect the p24 antigen to determine the presence of the HIV virus. Further assays can then be performed using FISH to determine the genetic composition of the HIV virus using fluorescently labeled oligonucleotide probes and the like.

One method of sample preparation is to react a sample or subsample with an agent the specifically interacts with a molecule in the sample. Examples of such agents include a monoclonal antibody, a polyclonal antiserum, or an oligonucleotide or polynucleotide. Interaction of the agent with its cognate or binding partner can be detected using an enzymatic reaction, such as alkaline phosphatase or glucose oxidase or peroxidase to convert a soluble colorless substrate linked to the agent to a colored insoluble precipitate, or by directly conjugating a dye or a fluorescent molecule to the probe. In one aspect of the disclosure a first agent is labeled with a non-fluorescent label (e.g., a substrate that gives rise to a precipitate) and a second agent is labeled with a fluorescent label. If the same sample is to be used for both non-fluorescent detection and fluorescent detection, the non-fluorescent label preferably does not interfere with the fluorescent emissions from the fluorescent label. Examples of non-fluorescent labels include enzymes that convert a soluble colorless substrate to a colored insoluble precipitate (e.g., alkaline phosphatase, glucose oxidase, or peroxidase). Other non-fluorescent agent include small molecule reagents that change color upon interaction with a particular chemical structure.

In one aspect of Fluorescent in situ Hybridization (FISH), a fluorescently labeled oligonucleotide (e.g., a DNA, a RNA, and a DNA-RNA molecule) is used as an agent. The fluorescently labeled oligonucleotide is contacted with a sample (e.g., a tissue sample) on a microscope slide. If the labeled oligonucleotide is complementary to a target nucleotide sequence in the sample on the slide, a bright spot will be seen when visualized on a microscope system comprising a fluorescent excitation light source. The intensity of the fluorescence will depend on a number of factors, such as the type of label, reaction conditions, amount of target in the sample, amount of oligonucleotide agent, and amount of label on the oligonucleotide agent. There are a number of methods, known in the art that can be used to increase the amount of label attached to an agent in order to make the detection easier. FISH has an advantage that individual cells containing a target nucleotide sequences of interest can be visualized in the context of the sample or tissue sample. As mentioned above, this can be important in testing for types of diseases and disorders including cancer in which a cancer cell might penetrate normal tissues.

A given fluorescent molecule is characterized by an excitation spectrum (sometimes referred to as an absorption spectrum) and an emission spectrum. When a fluorescent molecule is irradiated with light at a wavelength within the excitation spectrum, the molecule fluoresces, emitting light at wavelengths in the emission spectrum for that particular molecule. Thus when a sample is irradiated with excitation light at a wavelength that excites a certain fluorescent molecule, the sample containing the fluorescent molecule fluoresces. In some instances the light emanating from the sample and surrounding area may be filtered to reject light outside a given fluorescent agent's emission spectrum. Thus an image acquired from a sample contacted with an agent comprising a fluorescent label shows only objects of interest in the sample that bind or interact with the fluorescently labeled agent.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A computer implemented method of quantifying a color in a sample comprising multiple colors, the method comprising:
   measuring a first color channel value in a plurality of pixels from a plurality of separate control samples, each separate control sample comprising a single color of interest;
   defining a vector for each of the plurality of separate control samples, wherein each vector comprises an average of each first color channel value present in the plurality of separate control samples;
   defining a matrix based upon control measurements comprising each of the averages for each of the first color channels;
   defining a conversion matrix comprising the inverse of the matrix based upon the control measurements;
   measuring second color channel values in an image of an experimental sample comprising a plurality of colors of interest, each pixel of the image of the experimental sample comprising a plurality of second color channels; and
   calculating an amount of a color in the experimental sample by converting the second color channel values in the experimental sample using the conversion matrix.

2. The method of claim 1, wherein the second color channels comprise red, green, and blue.

3. The method of claim 1, wherein each separate control sample is stained with a single staining reagent to generate the color of interest.

4. The method of claim 1, wherein the experimental sample is stained with a plurality of stains to generate a plurality of colors of interest.

5. The method of claim 1, wherein the number of stains in an experimental sample are less than or equal to the number of color channels.

6. The method of claim 1, wherein an image of the experimental sample is displayed as a monochrome image.

7. The method of claim 1, further comprising setting all but one of the color channel values to zero (0), thereby determining the amount of a single color in the experimental sample.

8. The method of claim 1, further comprising rendering a digital display of the experimental sample.

9. A computer program on a non-transitory computer readable medium comprising instructions to cause a computer to:
   measure a first color channel value in a plurality of pixels from a plurality of separate control samples, each separate control sample comprising a single color of interest;
   define a vector for each of the plurality of separate control samples, wherein each vector comprises an average of each first color channel value present in the plurality of separate control samples;
   define a matrix based upon control measurements comprising each of the averages for each of the first color channels;
   define a conversion matrix comprising the inverse of the matrix based upon the control measurements;
   measure second color channel values in an image of an experimental sample comprising a plurality of colors of interest, each pixel of the image of the experimental sample comprising a plurality of second color channels;
   calculate an amount of a color in the experimental sample by converting the second color channel values in the experimental sample using the conversion matrix; and
   outputting the amount of the color in the experimental sample.

10. The computer readable program of claim 9, wherein the second color channels comprise red, green, and blue.

11. The computer readable program of claim 9, wherein each separate control sample is stained with a single staining reagent to generate a color of interest.

12. The computer readable program of claim 9, wherein the experimental sample is stained with a plurality of stains to generate a plurality of colors of interest.

13. The computer readable program of claim 9, wherein the number of stains in an experimental sample are less than or equal to the number of color channels.

14. The computer readable program of claim 9, wherein an image of the experimental sample is displayed as a monochrome image.

15. The computer readable program of claim 9, further comprising setting all but one of the color channel values to zero (0), thereby determining the amount of a single color in the experimental sample.

16. The computer readable program of claim 9, further comprising rendering a digital display of the experimental sample.

17. A machine vision system for automated analysis of a biological sample on a slide comprising:
   a computer comprising:
   a system processor;
   a computer program on a nontransitory computer readable medium, the computer program comprising an image algorithm comprising instructions to cause the computer to:
      measure a first color channel value in a plurality of pixels from a plurality of separate control samples, each separate control sample comprising a single color of interest;
      define a vector for each of the plurality of separate control samples, wherein each vector comprises an average of each first color channel value present in the plurality of separate control samples;
      define a matrix comprising each of the averages for each of the color channels;
      define a conversion matrix comprising the inverse of the matrix based upon the control measurements;
      measure second color channel values in an image of an experimental sample comprising a plurality of colors of interest, each pixel of the image of the experimental sample comprising a plurality of second color channels;

calculating an amount of a color in the experimental sample by converting the second color channel values in the experimental sample using the conversion matrix; and outputting the amount of a color in the experimental sample;

a monitor in communication with the computer, and an input device in communication with the computer;

an optical system in communication with the computer, comprising:

a stage;

an automated loading and unloading member for loading and unloading of a slide;

an identification member;

an optical sensing array in optical communication with the stage configured to acquire an image at a location on a slide and in electrical communication with the processor, a storage member for storing the location of a candidate object or area of interest; and a storage device for storing each image.

* * * * *